(12) United States Patent
Kuzma

(10) Patent No.: US 6,968,238 B1
(45) Date of Patent: Nov. 22, 2005

(54) METHOD FOR INSERTING COCHLEAR ELECTRODE AND INSERTION TOOL FOR USE THEREWITH

(76) Inventor: Janusz A. Kuzma, 7591 E. Ponderosa Cir., Parker, CO (US) 80138

( * ) Notice: Subject to any disclaimer, the term of this patent is extended or adjusted under 35 U.S.C. 154(b) by 79 days.

(21) Appl. No.: 10/635,768

(22) Filed: Aug. 5, 2003

Related U.S. Application Data

(63) Continuation of application No. 09/706,233, filed on Nov. 3, 2000, now abandoned, which is a continuation-in-part of application No. 09/559,606, filed on Apr. 27, 2000, now abandoned, which is a continuation-in-part of application No. 09/298,410, filed on Apr. 23, 1999, now Pat. No. 6,195,586, which is a continuation-in-part of application No. 09/140,034, filed on Aug. 26, 1998, now Pat. No. 6,038,484.

(51) Int. Cl.⁷ ................................................ A61N 1/05
(52) U.S. Cl. ......................... 607/137; 607/57; 600/379; 600/585; 606/129
(58) Field of Search ................... 607/137, 57; 600/379, 600/585; 606/129

(56) References Cited

U.S. PATENT DOCUMENTS

| | | | |
|---|---|---|---|
| 4,819,647 A | 4/1989 | Byers et al. | |
| 5,443,493 A | * 8/1995 | Byers et al. | 607/137 |
| 5,545,219 A | 8/1996 | Kuzma | |
| 5,578,084 A | 11/1996 | Kuzma et al. | |
| 5,603,726 A | 2/1997 | Schulman et al. | |
| 5,645,585 A | 7/1997 | Kuzma | |
| 5,653,742 A | 8/1997 | Parker et al. | |
| 5,999,859 A | 12/1999 | Jolly | |
| 6,038,484 A | 3/2000 | Kuzma | |
| 6,070,105 A | 5/2000 | Kuzma | |
| 6,078,841 A | 6/2000 | Kuzma | |
| 6,112,124 A | 8/2000 | Loeb | |
| 6,119,044 A | 9/2000 | Kuzma | |
| 6,125,302 A | 9/2000 | Kuzma | |
| 6,129,753 A | 10/2000 | Kuzma | |
| 6,149,657 A | 11/2000 | Kuzma | |
| 6,163,729 A | 12/2000 | Kuzma | |
| 6,195,586 B1 | 2/2001 | Kuzma | |

FOREIGN PATENT DOCUMENTS

| | | |
|---|---|---|
| WO | WO-89/00870 A1 | 2/1989 |
| WO | WO-00/45618 A3 | 8/2000 |
| WO | WO-00/45618 A2 | 8/2000 |
| WO | WO-00/71063 A1 | 11/2000 |

* cited by examiner

*Primary Examiner*—Shawntina Fuqua

(57) ABSTRACT

An implantable electrode system, adapted for insertion into a cochlea, includes an elongate electrode array stored within a sheath. The electrode array has a multiplicity of electrode contacts carried on a flexible elongate carrier, which carrier is adapted for insertion into one of the spiraling ducts, e.g., the scala tympani, of the cochlea, and further has longitudinal channel or lumen that passes therethrough. 3–6 mm from the distal end of the electrode array. To insert the electrode system into the cochlea, a stylet wire is inserted into the channel or lumen of the electrode array while the electrode array is held within the sheath. The sheath is then removed, and the electrode array is then gently guided and pushed through a cochleostomy into the cochlea by extending the stylet wire to a desired depth. As the electrode array is thus inserted into the cochlea, the stylet wire is retracted and the electrode array remains implanted within the cochlea.

6 Claims, 17 Drawing Sheets

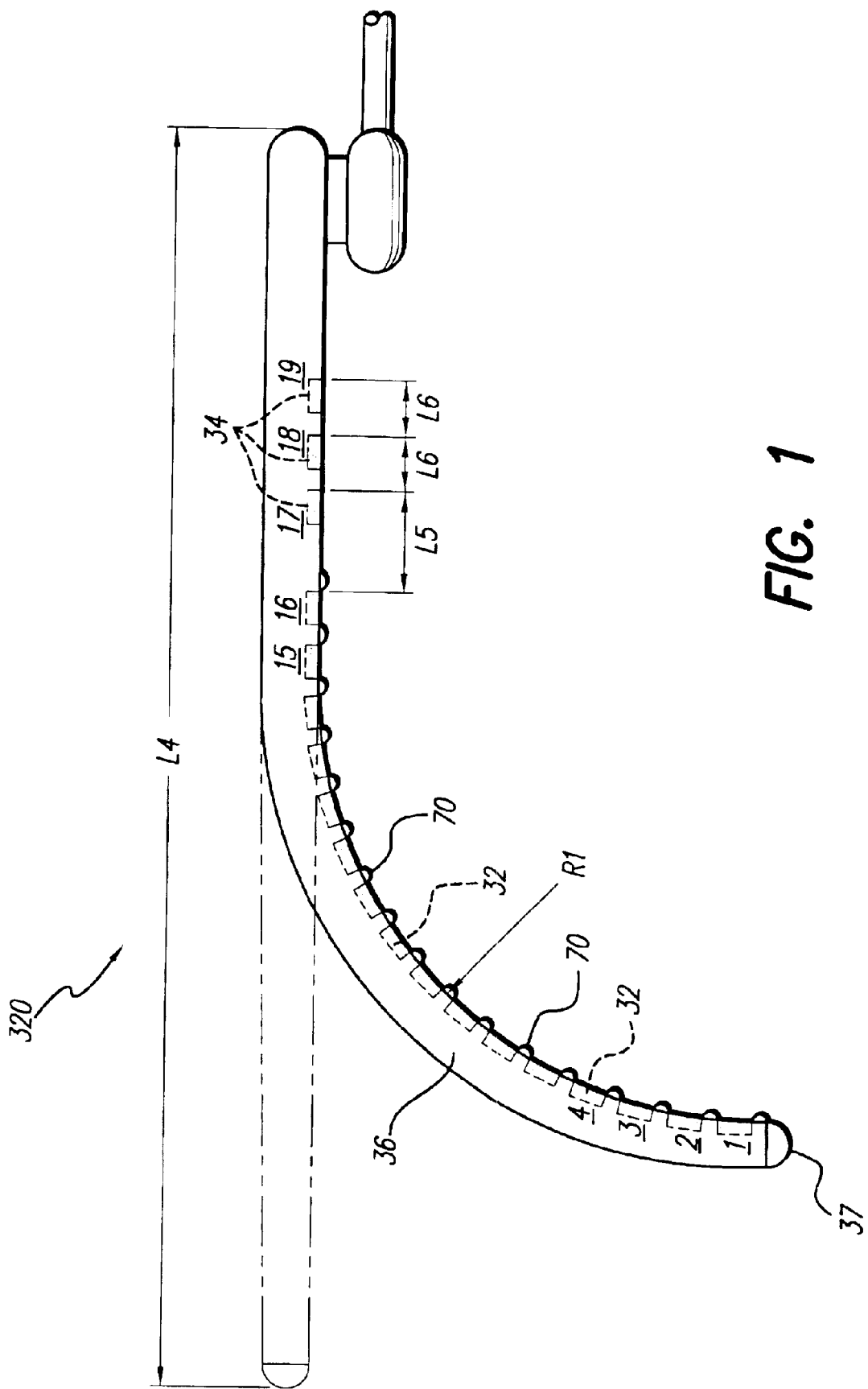

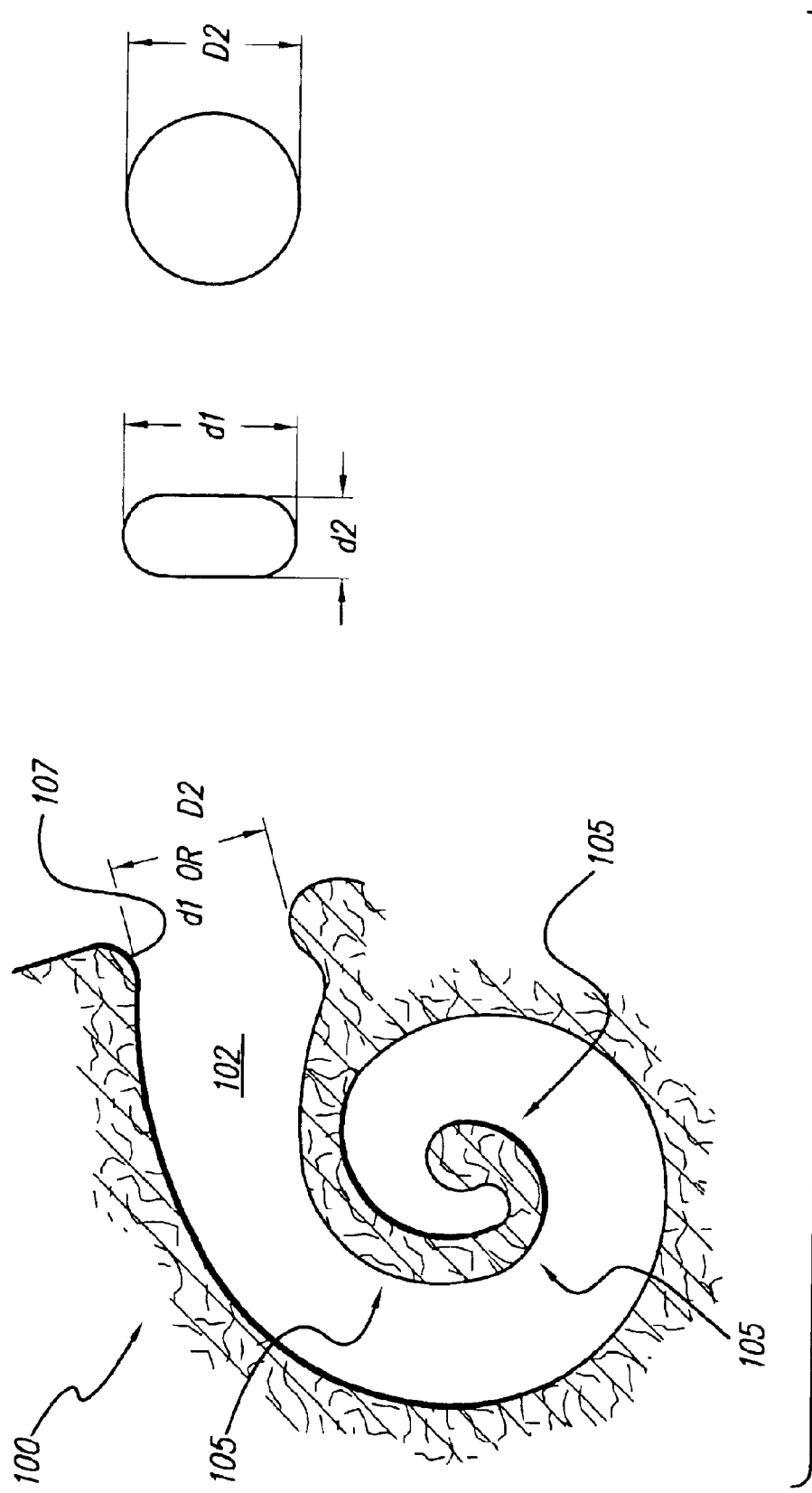

METHOD FOR INSERTING COCHLEAR ELECTRODE AND INSERTION TOOL FOR USE THEREWITH

The present application is a Continuation of U.S. application Ser. No. 09/706,233, filed Nov. 3, 2000 now abandoned, which application is a continuation-in-part (CIP) of U.S. application Ser. No. 09/559,606, filed Apr. 27, 2000 now abandoned; which is a CIP of application Ser. No. 09/298,410, filed Apr. 23, 1999, U.S. Pat. No. 6,195,586; which is a CIP of application Ser. No. 09/140,034, filed Aug. 26, 1998, U.S. Pat. No. 6,038,484; which patents and applications are incorporated herein by reference.

The subject matter of this application is closely related to the subject matter of U.S. application Ser. No. 09/443,628, filed Nov. 19, 1999, U.S. Pat. No. 6,321,125, which patent is also incorporated herein by reference.

BACKGROUND OF THE INVENTION

The present invention relates to implantable stimulation devices, e.g., cochlear prosthesis used to electrically stimulate the auditory nerve, and more particularly to an electrode array for use with a cochlear stimulator that is designed to hug the modiolus so as to place electrode contacts of the electrode array in close proximity to the ganglion cells and thereby to the auditory nerve fibers. Advantageously, such electrode array generally places the electrode contacts of the electrode array along one side of the array so that when the array is implanted within the cochlea, the side of the array whereon the electrode contacts are located can be positioned in close proximity to the ganglion cells that are to be stimulated, thereby allowing such ganglion cells to be stimulated with minimal power consumption. For example, where the array is implanted into the cochlea, the electrode side of the array may be positioned closest to the modiolar wall, thereby placing all of the individual electrode contacts in close proximity to the ganglion cells and thereby in close proximity to the auditory nerve fibers.

Hearing loss, which may be due to many different causes, is generally of two types: conductive and sensorineural. Of these, conductive hearing loss occurs where the normal mechanical pathways for sound to reach the hair cells in the cochlea are impeded, for example, by damage to the ossicles. Conductive hearing loss may often be helped by use of conventional hearing aids, which amplify sound so that acoustic information does reach the cochlea and the hair cells. Some types of conductive hearing loss are also amenable to alleviation by surgical procedures.

In many people who are profoundly deaf, however, the reason for their deafness is sensorineural hearing loss. This type of hearing loss is due to the absence or the destruction of the hair cells in the cochlea which are needed to transduce acoustic signals into auditory nerve impulses. These people are unable to derive any benefit from conventional hearing aid systems, no matter how loud the acoustic stimulus is made, because their mechanisms for transducing sound energy into auditory nerve impulses have been damaged. Thus, in the absence of properly functioning hair cells, there is no way auditory nerve impulses can be generated directly from sounds.

To overcome sensorineural deafness, there have been developed numerous cochlear implant systems—or cochlear prosthesis—which seek to bypass the hair cells in the cochlea (the hair cells are located in the vicinity of the radially outer wall of the cochlea) by presenting electrical stimulation to the auditory nerve fibers directly, leading to the perception of sound in the brain and at least partial restoration of hearing function. The common denominator in most of these cochlear prosthesis systems has been the implantation into the cochlea of electrodes which are responsive to a suitable external source of electrical stimuli and which are intended to transmit those stimuli to the ganglion cells and thereby to the auditory nerve fibers.

A cochlear prosthesis operates by direct electrical stimulation of the auditory nerve cells, bypassing the defective cochlear hair cells that normally transduce acoustic energy into electrical activity in such nerve cells. In addition to stimulating the nerve cells, the electronic circuitry and the electrode array of the cochlear prosthesis performs the function of the separating the acoustic signal into a number of parallel channels of information, each representing the intensity of a narrow band of frequencies within the acoustic spectrum. Ideally, each channel of information would be conveyed selectively to the subset of auditory nerve cells that normally transmitted information about that frequency band to the brain. Those nerve cells are arranged in an orderly tonotopic sequence, from high frequencies at the basal end of the cochlear spiral to progressively lower frequencies towards the apex. In practice, this goal tends to be difficult to realize because of the anatomy of the cochlea.

Over the past several years, a consensus has generally emerged that the scala tympani, one of the three parallel ducts that, in parallel, make up the spiral-shaped cochlea, provides the best location for implantation of an electrode array used with a cochlear prosthesis. The electrode array to be implanted in this site typically consists of a thin, elongated, flexible carrier containing several longitudinally disposed and separately connected stimulating electrode contacts, perhaps 6–30 in number. Such electrode array is pushed into the scala tympani duct to a depth of about 20–30 mm via a surgical opening made in the round window at the basal end of the duct. During use, electrical current is passed into the fluids and tissues immediately surrounding the individual electrode contacts in order to create transient potential gradients that, if sufficiently strong, cause the nearby auditory nerve fibers to generate action potentials. The auditory nerve fibers arise from cell bodies located in the spiral ganglion, which lies in the bone, or modiolus, adjacent to the scala tympani on the inside wall of its spiral course. Because the density of electrical current flowing through volume conductors such as tissues and fluids tends to be highest near the electrode contact that is the source of such current, stimulation at one contact site tends to activate selectively those spiral ganglion cells and their auditory nerve fibers that are closest to that contact site. Thus, there is a need for the electrode contacts to be positioned as close to the ganglion cells as possible. This means, in practice, that the electrode array, after implant, should preferably hug the modiolar wall, and that the individual electrodes of the electrode array should be positioned on or near that surface of the electrode array which is closest to the modiolar wall.

In order to address the above need, it is known in the art to make an intracochlear electrode array that includes a spiral-shaped resilient carrier which generally has a natural spiral shape so that it better conforms to the shape of the scala tympani. See, e.g., U.S. Pat. No. 4,819,647. The '647 U.S. patent is incorporated herein by reference. Unfortunately, while the electrode array with spiral-shaped carrier shown in the '647 patent represents a significant advance in the art, there exists lack of sufficient shape memory associated with the carrier to allow it to return to its original curvature (once having been straightened for initial insertion) with sufficient hugging force to allow it to wrap snugly against the modiolus of the cochlea.

It is also known in the art, as shown in applicant's prior patents, U.S. Pat. Nos. 5,545,219 and 5,645,585, to construct an electrode carrier from two initially straight members, a rodlike electrode carrier and a flexible rodlike positioning member. As shown in these patents, the two members extend in substantially parallel relation to and closely alongside each other, and remain connected to each other at least at their respective leading and trailing end regions. After implant, a pushing force is applied to the positioning member so that it is forced to assume an outwardly arched configuration relative to the electrode carrier, thereby forcing the electrode carrier into a close hugging engagement with the modiolus, thereby placing the electrode contacts of the electrodes in as close a juxtaposition to the cells of the spiral ganglion as possible. The '219 and '585 U.S. patents are also incorporated herein by reference. The '219 patent, in particular, provides in FIGS. 1–10 and accompanying text an excellent summary of prior art electrodes and the deficiencies associated therewith.

While the electrode array taught In the above-referenced '219 and '585 patents has the right idea, i.e., to force the electrode carrier into a close hugging engagement with the modiolus, it does so only by use of a system that makes manufacture of the lead more difficult and expensive, and only through application of an additional pushing force which is applied to an electrode structure after it is already fully inserted into the cochlea. Such additional pushing force may easily cause damage to the delicate scala tympani. Moreover, the entire electrode array may twist during the insertion process, or when the additional pushing force is applied, thereby causing the electrode contacts to twist and/or be forced away from the modiolus, rather than in a hugging relationship therewith.

Applicant's prior U.S. Patents e.g., U.S. Pat. Nos. 6,070,105 and 6,125,302, both of which are incorporated herein by reference disclose various other types of modiolar-hugging electrodes and systems that may be used to achieve the desired goal of placing the electrode contacts near the modiolar wall. In these applications, there is disclosed an electrode system that includes both an electrode array fashioned along a medial side of a flexible carrier and a flexible positioner, both of which are intended to be inserted into the scala tympani of a human cochlea. The flexible positioner acts as a spacer adapted to be inserted behind the electrode array so that its presence forces the electrode contacts near the modiolar wall. Disadvantageously, insertion of such system typically requires a two step insertion process (one step to insert the electrode array, and another step to insert the flexible positioner), and care must be exercised to assure that the flexible positioner does not slip to an incorrect position within the cochlea.

Thus, it is seen that while it is known that enhanced performance of a cochlear implant may be achieved by proper placement of the electrode contacts close to the modiolar wall of the cochlea, two main problems have faced designers in attempting to achieve this goal. First, it is extremely difficult to assemble electrode contacts on the medial side of the an electrode array, facing the modiolus of the cochlea. Second, heretofore there has either been the need for application of an external (and perhaps unsafe) force, or a lack of sufficient shape memory, to allow the electrode (after initial straightening to facilitate insertion) to assume or return to the desired curvature needed to place the electrodes against the modiolar wall so that the curvature wraps snugly around the modiolus of the cochlea. As a result, the electrode contacts of the prior art electrodes generally remain positioned too far way from the modiolar wall.

Many cochlear electrode arrays of the prior art are made for insertion into a left cochlea, or a right cochlea, depending upon the orientation of the electrode contacts one to another. It would be desirable for a universal electrode array to be made that could be used in either cochlea, left or right, without concern for whether the electrodes were orientated in a right or left side orientation.

It is thus evident that improvements are still needed in cochlear electrodes, particularly to facilitate assembling an electrode so that the electrode contacts are on the medial side of the electrode array, and to better assure that the electrode assumes a close hugging relationship with the modiolus once implantation of the electrode has occurred.

SUMMARY OF THE INVENTION

The present invention addresses the above and other needs by providing a universal electrode array system, adapted for insertion into either a left or right cochlea, which provides improved stability of electrode contact direction. Such universal electrode array system includes a cochlear electrode array, e.g., of the type disclosed in Applicant's U.S. Pat. No. 6,129,753, incorporated herein by reference, combined with an electrode positioner, e.g., a straightened version of the type disclosed in Applicant's U.S. Pat. No. 6,078,841, also incorporated herein by reference. Advantageously, in accordance with the present invention, such electrode array and positioner are combined as a single system, with a distal tip of the positioner being joined to the electrode array near the distal tip of the electrode array. Thus, as one of the elements is inserted into the scala tympani duct of the cochlea, the other element is carried with it, allowing both elements of the system to be jointly inserted into the cochlea during a single implant operation. Such insertion is facilitated using an easy-to-use insertion tool, which insertion tool also comprises part of the present invention.

In accordance with one aspect of the present invention, the electrode array component of the electrode system preferably has all of the electrode contacts spaced apart along one edge or side of the array, termed the "medial side". In a preferred embodiment, the structure of the electrode array facilitates bending of the array with the electrode contacts on the inside of the bend, yet deters flexing or twisting of the array that would tend to position or point the electrode contacts away from the inside of the bend. Hence, when inserted into the scala tympani duct of a cochlea, all of the electrode contacts on the medial side of the array generally face the modiolus wall of the cochlea.

In accordance with another aspect of the invention, small non-conductive bumps or humps may be formed in the electrode array between the electrode contact areas on the medial side of the array. These small bumps may be made, e.g., from a soft silicone rubber, or equivalent substance. When inserted into the cochlea, the small bumps serve as non-irritating stand-offs, or spacers, that keep the electrode contacts near the modiolus wall, but prevent the electrode contacts from actually touching the modiolus wall. These bumps also serve as dielectric insulators that help steer the stimulating electrical current in the desired direction, towards the modiolus wall, as taught, e.g., in U.S. Pat. No. 6,112,124, incorporated herein by reference.

In accordance with yet another aspect of the invention, a distal tip of the positioner, which forms one component of the electrode system, is attached at one point to the electrode array, another component of the electrode system, near, but not at, the distal tip of the electrode array. This allows the positioner, when inserted into the cochlea, to reside behind the electrode array, filling the space behind the electrode array, and forcing the electrode contacts of the electrode array to be positioned against or near the modiolus wall. Further, because the positioner is attached to the electrode array near the distal tip of the electrode array, the electrode array and positioner may be inserted into the cochlea at the same time using an appropriate insertion tool.

In accordance with a still further aspect of the invention, a preferred insertion tool uses a stylet wire that is threaded into a lumen or channel that passes longitudinally through the positioner. A specially configured guiding tube holds and maintains the positioner in its desired location along a back side of the electrode array (opposite the medial side) during the insertion procedure. The stylet wire, with the positioner component of the system threaded thereon, is gently guided and pushed, as required, in order to steer and slide the positioner, and the electrode array which is connected to it, into the scala tympani (or other duct) of the cochlea to the desired depth. Advantageously, the guiding tube holds the electrode array in a parallel position to the positioner during the initial placement of the electrode system within the cochlea, and in particular during the first 3–4 mm of advancement of the electrode system past the first turn of the scala tympani. Because the distal tip of the electrode array protrudes distally a short distance beyond the point where the distal tip of the positioner joins the electrode array, the protruding distal tip of the electrode array may function as a soft bumper as the electrode assembly is slid into and through the bends of the spiraling cochlea, thereby minimizing the risk of any serious damage or trauma to the cochlea or the patient as the implant operation is carried out.

In accordance with still a further aspect of the invention, both components of the electrode system of the present invention—the universal electrode array and the positioner—are manufactured using easy, low cost technology; and once made can be easily inserted, removed and reinserted, if required, into the cochlea or other curved body cavity.

Advantageously, the cochlear electrode system of the present invention achieves the following goals: (1) it assures that the electrode contacts of the electrode array are optimally positioned facing the medial direction, e.g., facing the modiolar wall in a cochlea of any size or any side (left or right) of the body; (2) it assures the electrode contacts, or alternatively the non-conductive humps or bumps (if used) between the electrode contacts, are positioned against the modiolar wall; (3) it may be manufactured using easy, low cost technology; (4) it may be easily inserted into the cochlea, and removed and reinserted, if required; and (5) it allows both the electrode array and positioner to be simultaneously inserted into the cochlea using a convenient simple-to-use insertion tool.

It is a feature of the present invention to provide a space-filling electrode system for use in a cochlea that positions the electrode contacts of an electrode array near the modiolar wall of the cochlea.

It is a further feature of the invention to provide an easy-to-use insertion tool that may be used to facilitate insertion of the space-filling electrode system into the cochlea with minimal effort and without serious risk of injury or trauma to the cochlea or the patient.

BRIEF DESCRIPTION OF THE DRAWINGS

The above and other aspects, features and advantages of the present invention will be more apparent from the following more particular description thereof, presented in conjunction with the following drawings wherein:

FIG. 1 illustrates a representative electrode array that may form one component of the present invention;

FIG. 4A is a longitudinal sectional view of the distal end of the embodiment of the electrode system of FIG. 4;

FIG. 5A is a cross-sectional view of the distal end of the embodiment of the electrode system of FIG. 5;

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

The invention described herein teaches a particular type of implantable electrode array system intended for use with a cochlear stimulation system. The electrode system of the present invention is designed to be inserted deep into the cochlea of the user of the cochlear stimulation system.

The electrode system of the present invention is made from two main components: (1) an electrode array having electrode contacts, and (2) a positioner joined at its distal tip to the electrode array near its distal tip. Because each of the components of the electrode system described herein may be made separately, and joined together later, and each component after being joined to the other continues to serve its separate function, it will first be instructive to describe each component separately, and the function served by each component, and then describe how the two components are joined together and inserted into the cochlea.

Figure 1A:
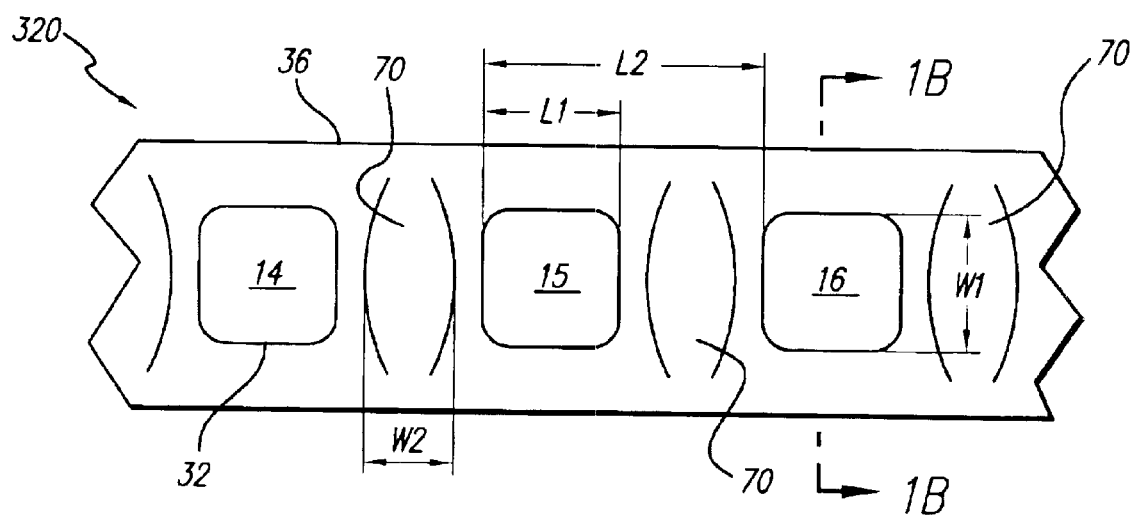
FIG. 1A depicts a representative portion of the medial side of the electrode array of FIG. 1.
Figure 1B:
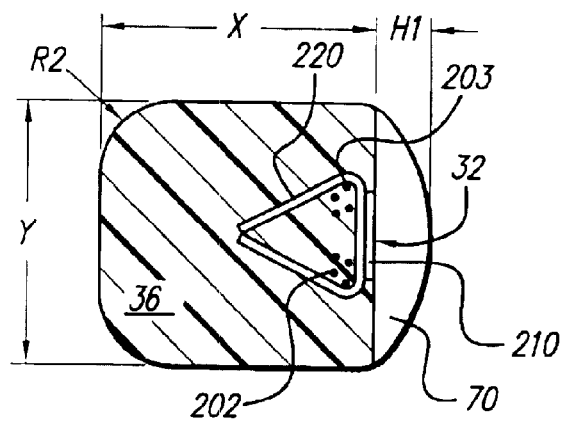
FIG. 1B shows a sectional view of the electrode array of FIG. 1A taken along the sectional line 1B—1B of FIG. 1A.

Accordingly, the description presented below in conjunction with FIGS. 1, 1A and 1B provides a brief overview of a representative electrode array 320 that may be used with the invention. Such electrode array is fully described in Applicant's earlier patent, U.S. Pat. No. 6,129,753, previously incorporated herein by reference. Similarly, the description presented below in conjunction with FIGS. 2A, 2B and 2C relates to a representative positioner 310 that may be used with the invention. Such positioner is of the type more fully described in Applicant's earlier patent, U.S. Pat. No. 6,078,841, also previously incorporated herein by reference, except that the positioner 310 is preferably formed in a relatively straight shape, whereas the positioner described in the '841 patent, in a preferred embodiment, is formed in a hooked shape.

Following the brief description of the positioner 310 and the electrode array 320, an electrode system 300, comprising a positioner 310 attached at its distal tip to an electrode array 320 near its distal tip, is described in conjunction with FIGS. 3, 4, 4A, 5 and 5A. This description includes a description of some representative ways (but certainly not the only ways) that the positioner may be attached to the electrode array. Then, a preferred technique for inserting the electrode system 300 into the cochlea is described in connection with FIGS. 6 through FIG. 18. Such insertion technique includes the use of an insertion tool 150 and a guiding tube 420.

It is to be emphasized that the description of the positioner 310 and the electrode array 320 is intended as a summary or overview, and that additional details associated with each component may be found in the referenced patents. Further, it should be noted that the positioner 310 and electrode array 320 described below, and in the referenced patents, are not intended to be limiting, but are only intended to be representative of an exemplary positioner(s) and electrode array (s) that could be used with the invention.

The electrode system of the present invention may be best used with an implantable multichannel pulse generator, e.g., an implantable cochlear stimulator (ICS) of the type disclosed in U.S. Pat. No. 5,603,726, incorporated herein by reference, or other suitable stimulator. It is to be understood, however, that although a cochlear electrode array is hereafter described, having dimensions suitable for insertion into the cochlea, the principles of the invention may be applied to other types of implantable leads for applications other than cochlear stimulation.

Unless noted otherwise, the materials from which the electrode system 320 of the invention is made, and the manner of making the electrode array, may be conventional, as are known in the art.

Turning first, then, to FIGS. 1, 1A and 1B, a brief description of the electrode array 320 will be presented. The electrode array 320 includes electrode array contacts 32 equally-spaced along a medial side of a flexible carrier 36. The flexible carrier 36 is made from LSR-70, or an equivalent biocompatible, flexible, nonconductive substance, and is molded around an assembly of electrode contacts 32 and interconnecting wires. LSR-70 or LSR-25, or equivalent materials, comprise a suitable biocompatible material commonly used with implantable leads and other implantable components. The properties of LSR-70 and LSR-25 are well known in the art, and LSR-70 and LSR-25 may be obtained commercially from numerous sources, LSR-70 is formed into a desired shape by injecting or otherwise inserting it into a mold while in a liquid state and allowing it to cure in the mold at a specified temperature for a specified time period. LSR-25 may likewise be formed into a desired shape using a similar molding process, or it may be applied through a suitable applicator, e.g, a syringe, to a desired area and then formed into a desired shape. LSR-25 is essentially the same as LSR-70 except that when it cures it is significantly softer, i.e., more pliable.

The electrode array 320 has an overall length L4. Such length L4 is most easily measured when the array 30 is straightened, as shown by the dotted lines in FIG. 1. In the preferred embodiment, L4 has a value of approximately 25 mm. The electrode array 30 may be formed to assume any desired shape. In one embodiment, for example, the electrode array 320 may be straight. In another embodiment, shown in FIG. 1, the electrode array is formed to Include a natural curve having a radius of curvature R1, with the electrode contacts 32 being positioned along the inside of the curve. The radius of curative R1 may have a value of approximately 9.0 mm.

As further seen in FIG. 1, a soft tip 37, may be included at the distal end of the carrier 36. When used, such tip 37 is typically formed from LSR-25 at the very distal tip of the electrode array 320.

As additionally illustrated in FIG. 1, reference marker contacts 34, identified as electrodes 17, 18 and 19, are spaced from the active electrode 16 a distance L5, with a spacing between the reference marker electrodes of L6. In the preferred embodiment, the distance L5 is about 3.0 mm, and the distance L6 is about 1.0 mm.

Referring next to FIG. 1A, the preferred spacing between the individual electrode contacts 32 is depicted. Such spacing, as well as all the other dimensional detail presented herein, is exemplary of a cochlear electrode, and is not intended to be limiting. As seen in FIG. 1A, each exposed electrode contact surface area comprises a generally rectangular-shaped area having a length L1 and a width W1. Other shapes could also be used. In the preferred embodiment, the rectangular area is roughly a square, with L1 and W1 each having a value of approximately 0.4 mm ±10%, thereby providing an exposed electrode surface area of approximately 0.16 mm$^2$. The spacing between corresponding points of adjacent electrode contact areas 32 is a distance L2. L2 has a nominal value of approximately 0.9 mm ±0.1 mm.

Still with reference to FIGS. 1 and 1A, a series of small non-conductive bumps, or humps 70, may, in accordance with one embodiment of the electrode array, be formed between the electrode contact areas 32. As seen best in FIG. 1B, these humps 70 have a height H1 of about 0.13 mm, and as seen best in FIG. 1A, have a width W2 of about 0.25 mm. As further seen best in FIG. 1, the humps 70 extend out from the medial surface of the electrode array. The humps 70 are made preferably from a soft silicone rubber, or equivalent substance, such as LSR-25, although in some embodiments they may be made from LSR-70. When inserted into the cochlea, the small bumps 70 serve as non-irritating stand-offs, or spacers, that allow the electrode contacts 32 to be positioned near the modiolar wall, but prevent the electrode contacts 32 from actually touching the modiolar wall. The humps 70 further serve as dielectric insulators that help steer the stimulating electrical current, flowing to or from the electrode contacts, in the desired direction, from or towards the cells located in the modiolar wall, as taught, e.g., in the previously referenced U.S. Pat. No. 6,112,124.

The electrode contact areas comprise an exposed surface of an electrode contact 32 that is formed from folded strips 210 and 220 of a biocompatible metal, such as platinum, as described more fully in '753 patent. Such electrode contacts are embedded within the molded carrier 36 as illustrated in the sectional view of FIG. 1B, which is taken along the lines 1B—1B of FIG. 1A. As seen in FIG. 1B, the carrier 36 is formed to have a cross-sectional area that is generally rectangular, having dimensions of X by Y mm, where the values of X and Y vary as a function of where along the length of the carrier the cross section is viewed. At electrode 16 (near the proximal end of the electrode/array 320), for example, X and Y are both about 0.8 mm. At electrode 1 (near the distal tip of the electrode array), X and Y are both about 0.6 mm. Thus, it is seen that for the embodiment shown in FIGS. 1, the carrier 36 is tapered along its length so that it has a smaller cross section at its distal tip than it does at its proximal end. Such tapering, however, is not required in order to practice the invention.

Still with reference to the cross-sectional view of the array shown in FIG. 1B, it is seen that the sectional shape has rounded corners on the side opposite the medial side. (As explained previously, the medial side is the side where the electrode contacts 32 are located.) The rounded corners have a radius of curvature R2 that is approximately 0.3 mm in the preferred embodiment.

The electrode contacts 32 have a general cross sectional shape, as seen in FIG. 1B that resembles a triangle. The base of this triangular-shaped (or "Δ-shaped") electrode forms the exposed electrode contact area along the medial side of the electrode array, e.g., as seen in FIG. 1. The upward sloping legs 220 of this Δ-shape electrode extend into the body of the carrier 36, e.g., as anchors, and thus become embedded (non-exposed) portions of the electrodes. It should be noted that while in the preferred embodiment the upward sloping legs 220 touch at their respective tips to form the Δ shape, such touching is not required; nor is the Δ shape required. What is important is that these legs 220 extend into the body of the carrier, in some fashion, so that the electrode is firmly anchored in its desired position along the length of the carrier. For example, in some embodiments, the legs 220 may be completely folded over so as to lie almost flat on top of the exposed surface area. In other embodiments, the legs 220 may extend more or less straight into the body of the carrier, forming a generally "U" cross-sectional shape.

Wire bundles 202 and 203 pass through the corners of the Δ-shaped (or other-shaped) electrodes and become embedded within the molded carrier 36 when formed.

Figure 2A:
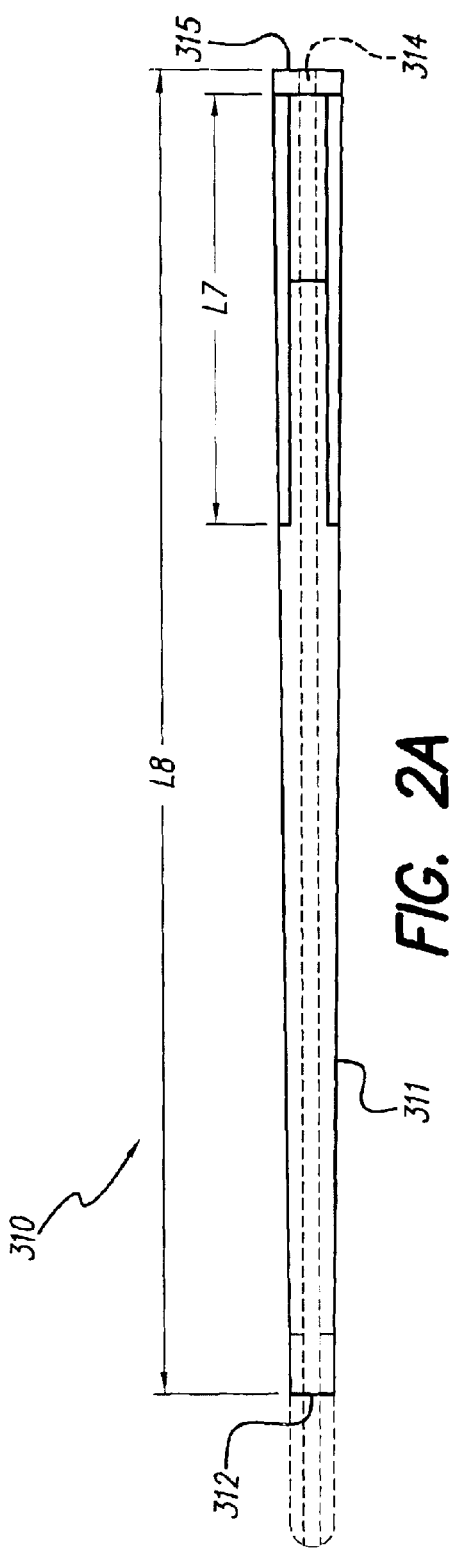
FIGS. 2A and 2B illustrate, respectively, a bottom and side view of a positioner, which positioner forms another component of the present invention.
Figure 2B:
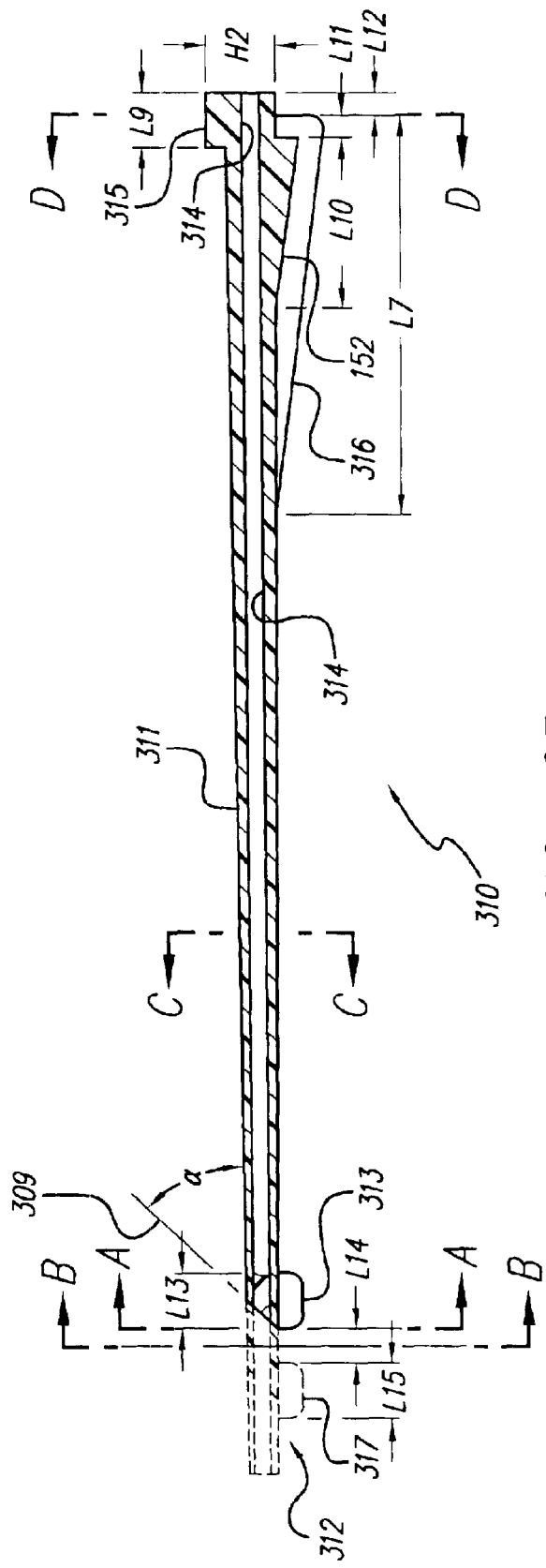
Figure 2C:
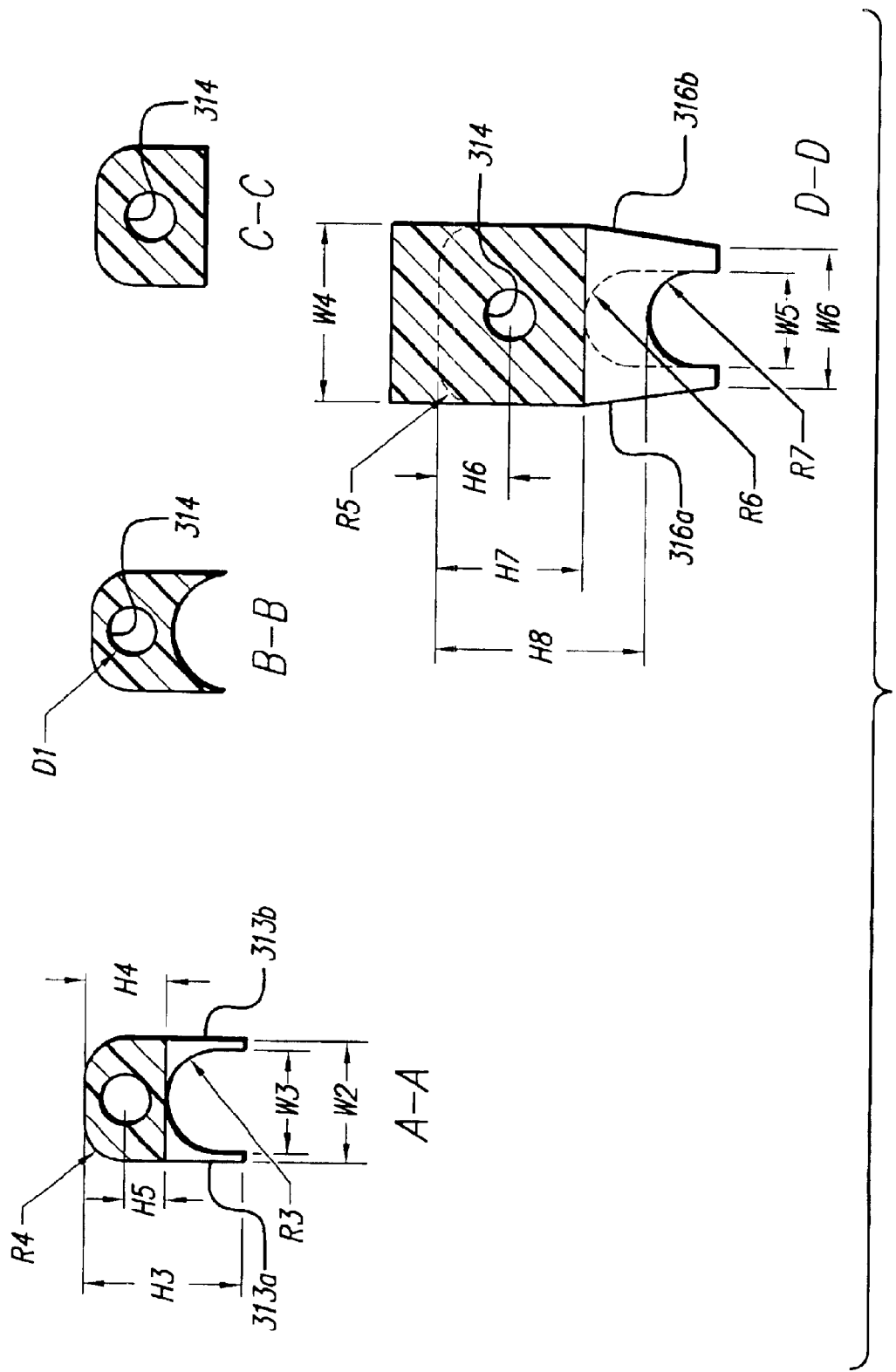
FIG. 2C shows four representative sectional views of the positioner of FIG. 2B, taken respectively at section lines A—A, B—B, C—C and D—D of the positioner of FIG. 2B.

Next, with reference to FIGS. 2A, 2B and 2C, a brief description of the positioner 310 will be provided. FIGS. 2A and 2B illustrate, respectively, a bottom and side view of the positioner 310, and FIG. 2C shows four representative sectional views of the positioner 310, taken respectively at section lines A—A, B—B, C—C and D—D of the positioner 310 shown in FIG. 2B.

The positioner 310 is formed from a suitable silicone polymer In a relatively straight shape, forming an elongate flexible member. Typically, the positioner is made using a silastic tube and molding an appropriate silicone polymer around the tube. The entire positioner is best seen in FIGS. 2A and 2B. Such flexible member has a distal tip 312 and a proximal end 315. A first pair of keeper tabs 313, comprising tabs 313a and 313b (sometimes referred to as "keeper wings", or just "wings"), protrude from the positioner in the vicinity of its distal tip. A first tab 313a of the first pair of tabs 313 is adapted to lie against one side of the electrode array near the distal end of the array. The other tab 313b of the first pair of keep tabs 313 is similarly adapted to lie against an opposite side of the electrode array. The space between the tabs 313a and 313b thus defines a distal channel wherein the distal end of the electrode array may be placed. This distal channel helps hold the distal end of the positioner 310 in its desired position alongside the distal end of the electrode array when the electrode system 300 is inserted into the cochlea.

A second pair of keeper tabs 317 protrude from the positioner at a location that is near the location where the first pair of keeper tabs 313 protrude, but closer to the distal end of the positioner 310. A first tab of the second pair of tabs 317 is adapted to lie against one side of the electrode array, and the other tab of the second pair of keeper tabs 317 is similarly adapted to lie against an opposite side of the electrode array. The space between the tabs thus further defines the distal channel wherein the distal end of the electrode array may be placed. The second pair of tabs 317 may be trimmed off by cutting the positioner material 311 along a trim line 309, if desired. If both pairs of tabs 313 and 317 are desired, then the trim line is moved distally so that both pairs of tabs remain after trimming.

The first pair of keeper tabs 313, as well as the second pair of keeper tabs 317, when used, are formed of the same material as the elongate flexible member 311 that makes up the positioner 310. As a result, the keeper tab pairs 313 and 317 are also flexible, forming an integral part of the flexible member 311 that makes up the positioner 310.

The positioner 310 further includes a pair of side walls 316 protruding from the proximal end 315 of the positioner 310. One side wall 316a of the pair of side walls 316 is adapted to lie against one side of the proximal end of the electrode array, and the other side wall 316b of the pair of side walls 316 is adapted to lie against an opposite side of the proximal end of the electrode array. The space between the side walls 316a and 316b thus defines a proximal channel adapted to receive a corresponding proximal end of the electrode array 320. This proximal channel is adapted to keep the proximal end of the positioner alongside the proximal end of the electrode array when the electrode system 300 is inserted into the cochlea.

A lumen or passageway 314, having a diameter D1, is formed to pass longitudinally through the body of the positioner 310. This lumen or passageway 314 is closed at the distal end of the positioner. In one embodiment, a marker, i.e., a metal ball, may be inserted into the closed end of the passageway 314 of the positioner 310 to facilitate viewing the location of the distal tip of the positioner with an imaging system, e.g., an X-ray system. During insertion, the lumen or passageway 314 is adapted to receive a stylet wire, as will be explained hereinafter. The stylet wire is used as part of a tool during the insertion process to facilitate insertion of the electrode system 300 into the scala tympani of the cochlea.

The positioner 310 has a sloping floor 152 in the bottom of the electrode channel located between the side walls 316 at the proximal end 315 of the positioner 310. The slope associated with this sloping floor is the distance between the height H8 and the height H7, seen at the sectional-line D—D in FIG. 2C. As seen best in FIGS. 2B and 2C, the pair of proximal side walls 316, comprising a right side wall 316b and a left side wall 316a (as viewed in FIG. 2C), have a varying height that, when viewed in the side view of FIG. 2B causes an upper edge of each side wall to slope from a maximum height at the extreme proximal end of the positioner (at sectional line D—D in FIG. 2C) to a zero height, or near zero height, at a location that is a distance L7 from the sectional line D—D. The sloping floor 152 has a length of L10.

The overall thickness of the positioner 310 at the proximal end of the positioner, i.e., at the sectional line D—D, narrows towards the distal end of the positioner, as seen best in the sectional views of FIG. 2C. That is, as seen in FIG. 2C, the thickness H7 at the sectional line D—D at the proximal end of the positioner is greater than the thickness H4 at the sectional line A—A at the distal end of the positioner. Similarly, the width W4 at the proximal end is greater than the width W2 at the distal end. Representative values for the dimensions W2 and W4, as well as other dimensions shown in FIGS. 2A, 2B and 2C, are shown in Table 1 below.

As further seen at section line D—D in FIG. 2C, the side walls 316 of the positioner 310 have exterior walls that are thicker near the main body of the positioner than they are at a top edge. That is, as seen in FIG. 2C, the width of the positioner is W4 at the proximal end (at section line D—D) of the positioner, and this also is the distance between the exterior edges of the side walls 316 at a base of the side walls. At the top edge of the side walls, however, the distance between the exterior edges of the side walls is W6, which is less than W4 as indicated in Table 1. The distance between the interior walls of the side walls W5, however, does not change from the base to the top.

TABLE 1

Representative Dimensions of Positioner 310 (FIGS. 2A, 2B and 2C)

| Dimension | Typical Value (mm) | Dimension | Typical Value (mm) |
|---|---|---|---|
| L7 | 7.0 | H6 | 0.45 |
| L8 | 23.8 ± 0.2 | H7 | 0.90 |
| L9 | 1.0 | H8 | 1.30 |
| L10 | 3.0 | D1 | 0.30 |
| L11 | 0.4 | W2 | 0.70 |
| L12 | 0.4 | W3 | 0.60 |
| L13 | 1.0 ± 0.2 | W4 | 1.10 |
| L14 | 0.5 | W5 | 0.60 |
| L15 | 1.0 | W6 | 0.85 |
| H2 | 1.2 ± 0.1 | R3 | 0.30 |

TABLE 1-continued

Representative Dimensions of Positioner 310 (FIGS. 2A, 2B and 2C)

| Dimension | Typical Value (mm) | Dimension | Typical Value (mm) |
|---|---|---|---|
| H3 | 0.95 | R4 | 0.25 |
| H4 | 0.5 | R5 | 0.40 |
| H5 | 0.25 | R6=R7 | 0.25 |

Figure 3:
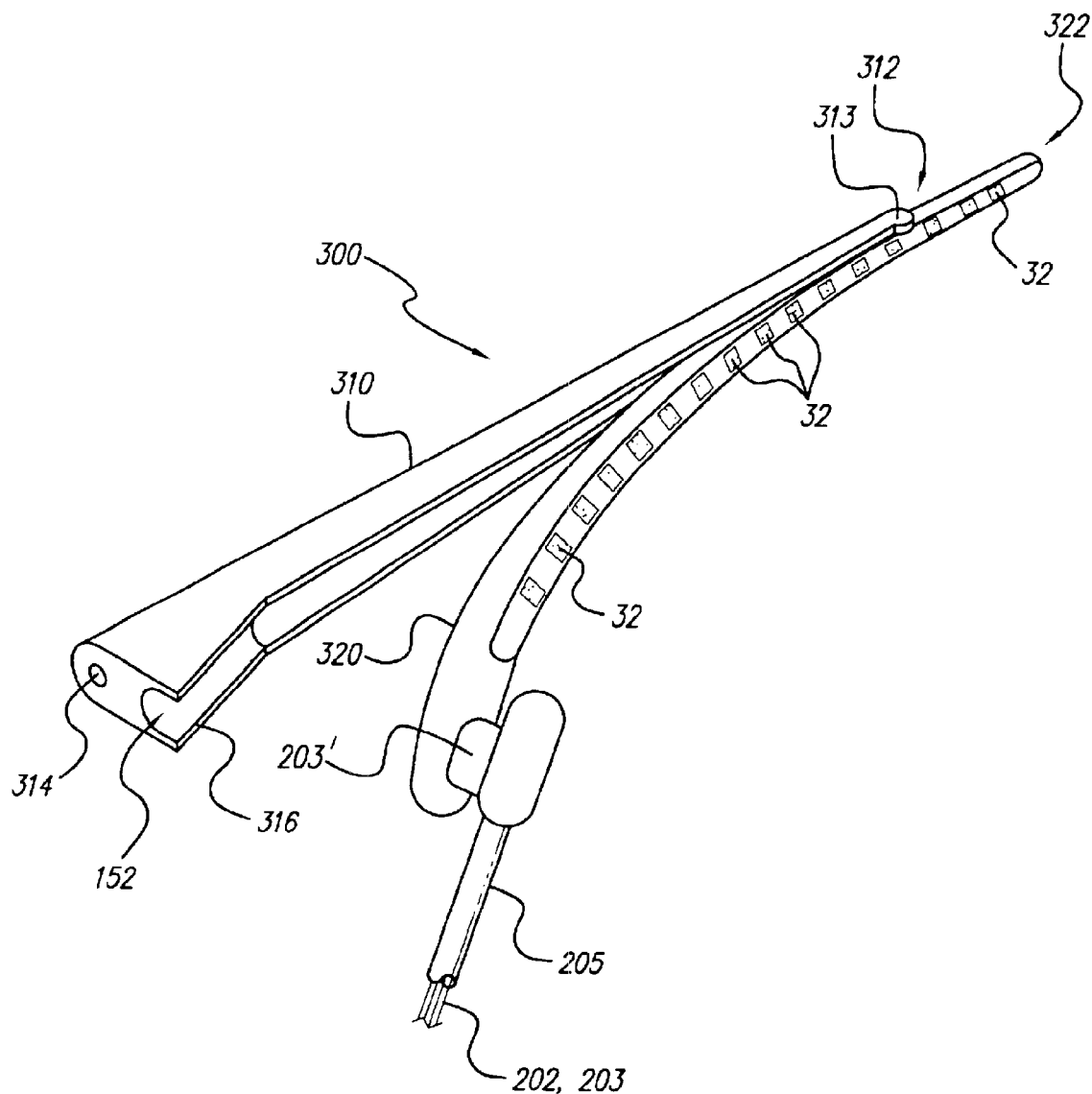
FIG. 3 illustrates the electrode system of the present invention which comprises a positioner joined to an electrode array at or near the distal tip of the electrode array.

An electrode system 300 made in accordance with the present invention combines the positioner 310 with the electrode array 320 as depicted in FIG. 3. More particularly, the distal tip 312 of the positioner 310 is glued, or otherwise affixed to, the electrode array 320 near the distal Tip of the array 320. Except for this one connection or attachment point, the electrode array 320, and the positioner 310, remain the same as described separately above.

The preferred location for affixing the distal tip 312 of the positioner 310 to the electrode array 320 is near the fourth or fifth most-distal electrodes 32 of the array (corresponding to electrodes 4 or 5 of the array), a distance of between about 3 to 6 mm from the distal tip of the electrode array. In one preferred embodiment, the location where the distal tip 312 of the positioner is affixed to the electrode array is over the fifth electrode. For a cochlear electrode, the attachment point of the distal tip 312 of the positioner 310 is thus about 4.5 mm from the distal tip of the electrode array 320.

Turning next to FIG. 3, an electrode system 300 made in accordance with the invention is shown. The electrode system 300 includes an electrode array 320 and a positioner 310. The positioner 310 of the electrode system 300 has its distal end 312 attached in some manner to the electrode array 320 at a point near, but not at, the distal tip of the electrode array. The electrode array 320 is an electrode array substantially the same as previously described in FIGS. 1, 1A and 1B, or as described in the referenced patents (see, e.g., U.S. Pat. No. 6,129,753). As previously described, In a preferred embodiment, the electrode array 320 includes a plurality of spaced-apart electrode contacts 32 along one side of a flexible carrier 36. The side on which the electrode contacts are located, or the side on which at least a portion of each electrode is exposed, is the side adapted to face the modiolar wall of a cochlea. Wires 202, 203 carried within the carrier of the electrode array, make electrical contact with various ones of the electrode contacts 32. An offset 203', near a proximal end of the electrode array 320, functions as a stop that prevents the electrode array from being inserted too deep into the cochlea, and further identifies the front side of the electrode array, i.e., identifies the side of the electrode array on which the electrode contacts 32 are exposed. A lead 205 extends from the offset 203' and carries the wires 202, 203 (which are encased within the lead 205) to a suitable proximal connector (not shown) or other destination where the wires 202, 203 are connected to appropriate electrical circuitry (not shown).

The positioner 310 is also substantially the same as previously described, e.g., substantially the same as the positioner described in connection with FIGS. 2A, 2B and 2C, or substantially the same as the positioner described in the referenced patents (see, e.g., U.S. Pat. No. 6,078,841). The positioner 310 is attached at its distal tip 312 to the electrode array 320. The point of attachment, i.e., the location where the distal tip 312 of the positioner 310 attaches to the electrode array 320, is about 3–5 mm from the distal end 322 of the electrode array. For the spacing of the electrode contacts 32 of an electrode of the type disclosed in the referenced '753 patent, this distance corresponds to a location that is about 3 or 4 contacts from the distal end 322 of the electrode array.

The manner used to attach the distal tip 312 of the positioner 310 to the electrode array 320 near its distal end 322 may vary. That is, the manner of attachment is not as important as the fact that an attachment of some kind be employed so that the positioner remains attached to the electrode array during and the insertion process.

Figure 4:
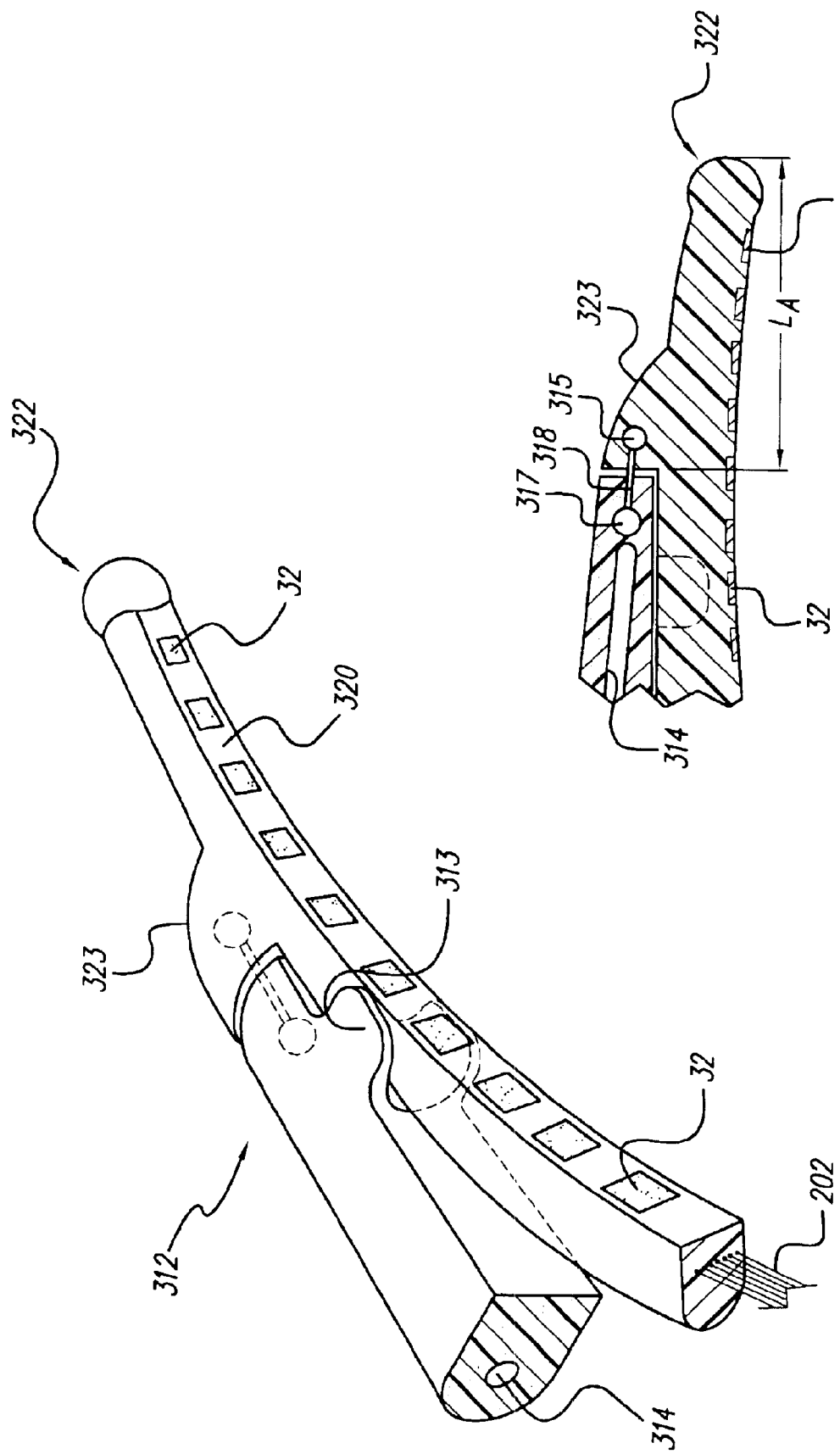
FIG. 4 shows a detailed view of the distal end of one alternative embodiment of the electrode system of the present invention at the point where the distal tip of the positioner is joined to the electrode array.

One way in which the attachment may be carried out is depicted in FIGS. 4 and 4A. A hump 323 is formed on the back side (the side opposite the electrode contacts 32) of the electrode array 320. The distal tip 312 of the positioner 310 abuts against a proximally-facing side of the hump 323. A ball 315 is embedded within the hump 323. A wire 318 is attached to the ball 314 and protrudes through the proximally-facing side of the hump 323 into the distal end 312 of the positioner 310. The other end of the wire 318 attaches to a second ball 317 embedded within the distal tip 312 of the positioner. Generally, the ball 317 is larger than the ball 315. To make the attachment, the ball 317 may be molded into a lumen 314 that passes through the positioner. The smaller ball 315, attached to the wire 318, may then be forced into a socket formed within the hump 323 of the electrode array. The distance $L_A$ from the distal tip 322 of the electrode array to the distal tip 312 of the positioner is about 3–5 mm. At least one pair of keeper tabs 313, or wings 313, are formed into the distal end of the positioner in order to form a channel into which the electrode array may pass, thereby keeping the positioner 310 in a desired alignment position alongside the electrode array 320. The electrode array 320 and positioner 310 may be made from any suitable materials as previously described, or as is known in the art. Typically, both the carrier of the electrode array 320 and the flexible positioner will be made from a suitable silicone polymer, such as LSR-70 and/or LSR-25. The balls 315 and 317, and the wire 318, may be made from platinum, or other suitable material.

Figure 5:
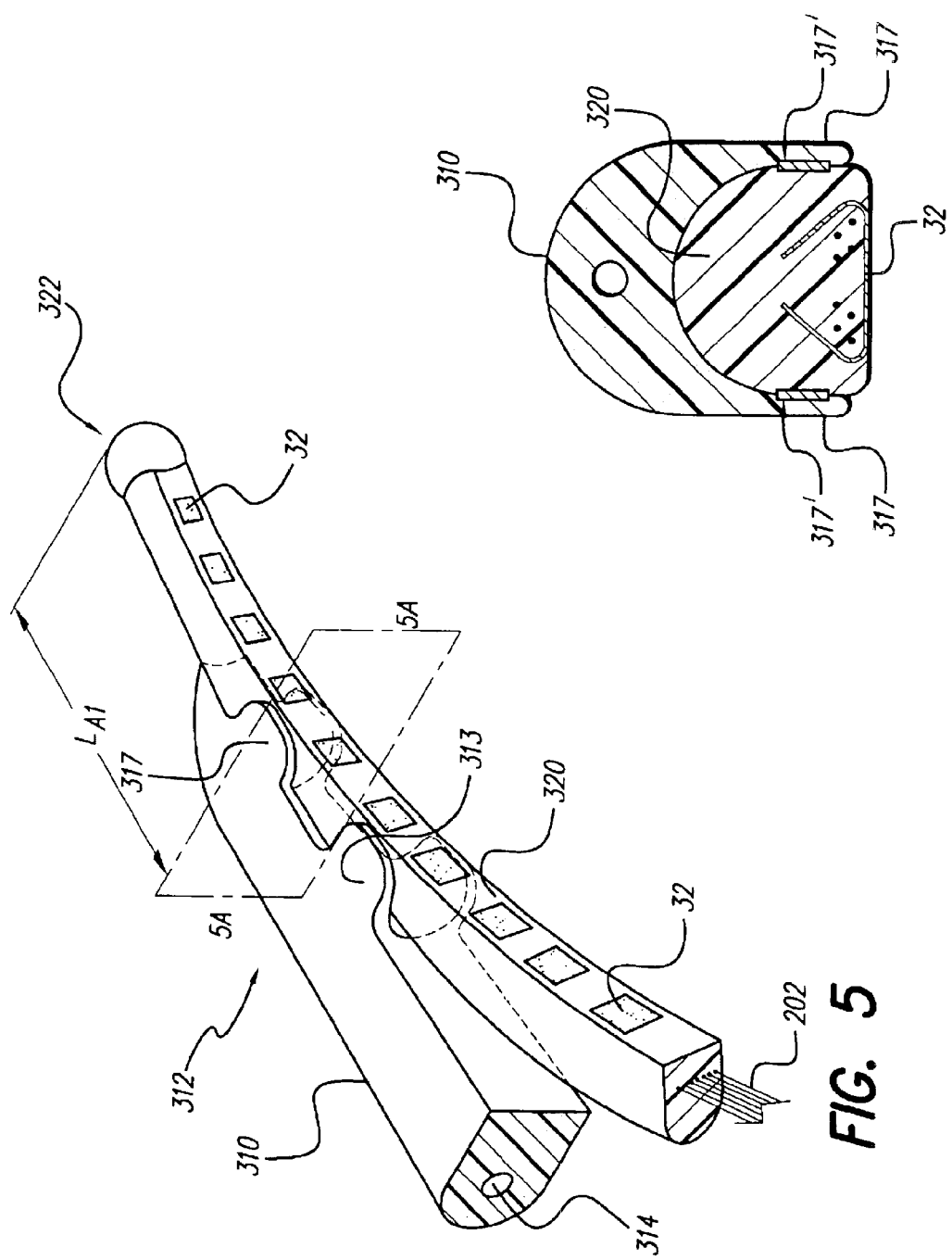
FIG. 5 illustrates a detailed view of the distal end of another alternative embodiment of the electrode system of the present invention at the point where the distal tip of the positioner is joined to the electrode array.

Turning next to FIGS. 5 and 5A, another technique for attaching the distal end 312 of the positioner 310 to the electrode array 320 is illustrated. The positioner 310 shown in FIGS. 5 and 5A includes a first pair of wings 317 (or keeper tabs) located at its distal tip 312. These wings 317 are placed over the sides of the electrode array 320 at a position that is a distance $L_{A1}$ from the distal tip 322 of the electrode array. Typically, the distance $L_{A1}$ is about 3–5 mm. The inside of both wings 317 is glued, or otherwise attached, to the electrode array 320 at connection points 317' using a suitable bonding agent. The connection points 317' may be realized using just a drop or two of a suitable glue, or equivalent substance, e.g., LSR-25 (while in a liquid state) which thereafter is allowed to cure. It is desirable to form the connection points 317' so that they will break lose at a specified force, thereby allowing the positioner to be forcibly removed from the electrode array should the need arise to make such detachment, and with the break point always occurring at the attachment points 317'.

As seen in FIG. 5, the positioner 310 may also include a second pair of wings 313, or keeper taps, that are positioned 1–2 mm more proximally than the first pair of wings, or keeper tabs, 317. Such second pair of wings 313, when used, may or may not be attached to the electrode array 320. If not attached to the electrode array, such tabs 313 still serve a keeping function, i.e., they help keep the positioner 310 in its desired position along the back side of the electrode array 320.

Figure 6:
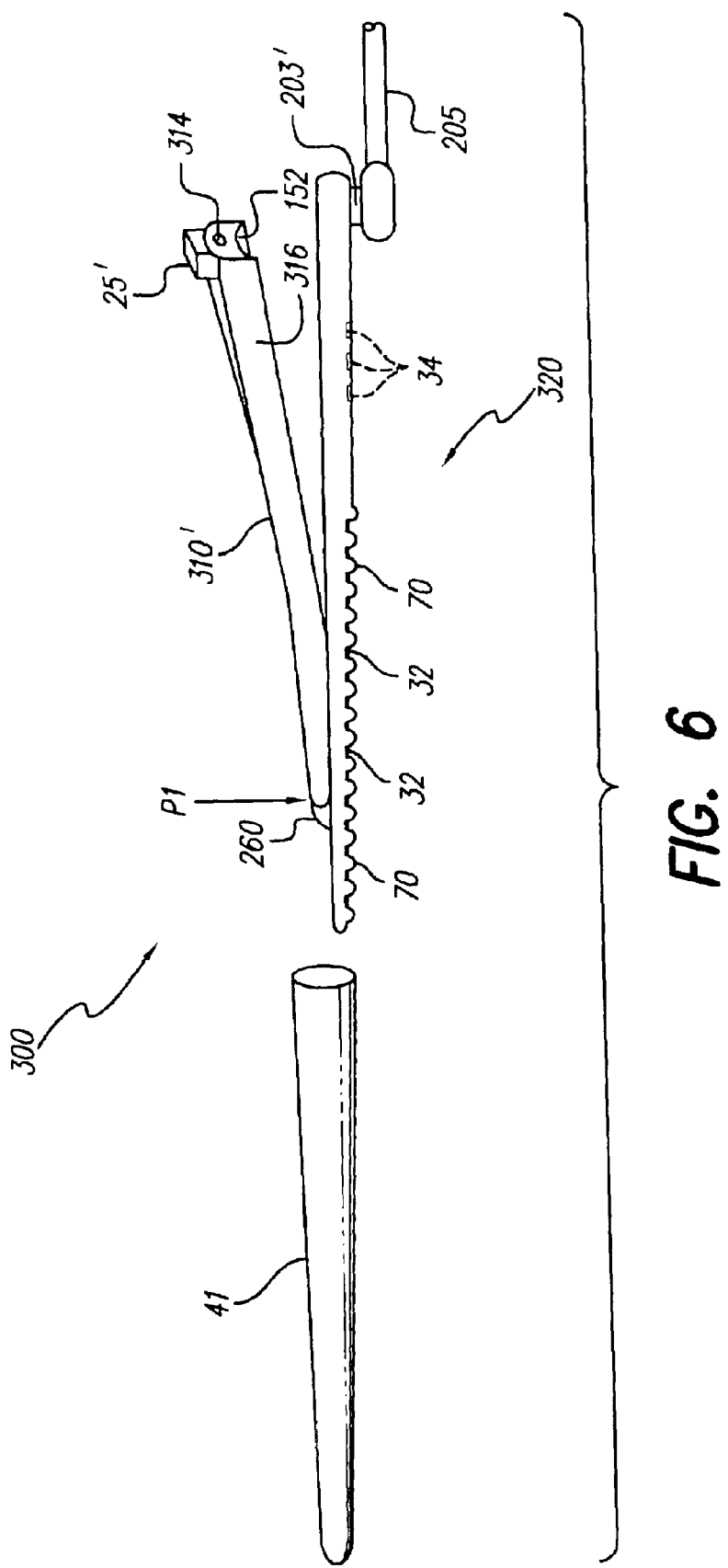
FIG. 6 is an exploded view of another embodiment of the electrode system of the present invention and further illustrates a sheath used to initially hold the positioner and the electrode array prior to insertion of the electrode system into the cochlea FIG. 7A schematically illustrates making a cochleostomy to gain access to the scala tympani of the cochlea, and further illustrates two possible shapes of the cochleostomy.

Turning next to FIG. 6, a side view of the main components of an electrode system 300 made in accordance with one embodiment of the invention are illustrated. The assembly includes an electrode array 320, the same or similar to that shown in FIG. 1. Such electrode array 320 includes a plurality, e.g., sixteen, spaced-apart electrode contacts 32, separated by a small hump 70. A few, e.g., three, spaced-apart reference electrode contacts 34 may also be located near the proximal end of the electrode array. A positioner 310', the same as or similar to the one shown in FIGS. 2A, 2B and 2C, is attached to the electrode array at a location P1. The positioner 310' includes a lumen or opening 314 that passes longitudinally through the body of the positioner. As shown in FIG. 6, the location P1 where the attachment occurs is on the back side of the array approximately opposite the fourth or fifth most distal electrode contact 32. The positioner 310' includes a proximal tab 25' that is located on the side of the positioner opposite the sloping channel floor 152.

As suggested in FIG. 6, another way to attach the distal tip 312 of the positioner 310' to the electrode array 320 is to glue the tip 312 to the body of the electrode array using a suitable silicone adhesive 260. For example, a silicone adhesive known as Silastic "A", commercially available from Dow Corning Chemical Company, may be used for this purpose. Alternatively, a drop or two of LSR-70 or LSR-25 placed at the distal tip of the positioner 310' while it is held in contact with the electrode array 320 at the desired attachment location P1, e.g., over the fourth or fifth electrode, may also be used for this purpose.

In connecting the distal tip 312 of the positioner 310' to the body of the electrode array 320, it may also be desirable to apply a suitable adhesive 260 to the surface of the electrode array and the distal tip of the positioner, as required, to fill and smooth the space between the distal tip 312 and the surface of the electrode body.

In order to strengthen the attachment of the distal tip 312 to the electrode array 320, particularly when under a compressive force, i.e., when pushing on the positioner from a proximal to a distal direction (as would occur when pushing the electrode assembly into the cochlea), a pin with a head may be inserted at the end of the channel 314 that passes longitudinally through the positioner 310'. The body of such pin would then extend into the adhesive 260, and provide additional structure to which the adhesive may bond in order to form a stronger bond. Such pin structure would make the joint formed between the distal tip of the positioner and the electrode array very secure when pushing on the positioner (applying a compressive force), as occurs when inserting the electrode system 300 into the cochlea. On the other hand, should the need arise to remove the positioner, the adhesive bond formed between the distal tip of the positioner and the electrode array 300 may generally be broken, or pulled apart, by pulling on the positioner (applying a tension force).

Still with reference to FIG. 6, it is seen that the electrode system 300 further includes a sheath 41 into which the electrode array 320, with positioner 310' attached thereto at point P1, is inserted. The sheath 41 is preferably made from plastic, and is used by the surgeon, or other medical personnel, during the insertion process to help hold the electrode system as a positioning wire or stylet is threaded into the opening 314. Once the stylet has been threaded into the opening 314, the sheath 41 may be pulled off of the electrode system and the sheath 41 may be discarded, as explained more fully below.

A significant advantage associated with use of the electrode system 300 is that the electrode system may be inserted into the scala tympani of the cochlea in a one step operation.

This is in contrast to the other electrode systems which usually require at least two steps (one step to insert the electrode, and another step to insert the positioner). The manner in which the one-step insertion is performed is illustrated in FIGS. 10 through 18. Before describing this insertion process, however, it will be helpful to first describe the insertion tools that are used to assist in the insertion process.

First, with respect to FIG. 7A, a schematic sectional view of the scala tympani 102 of a cochlea 100 is represented. It is the main purpose of the invention to provide an electrode array 320 that can be inserted into the scala tympani 102 of the cochlea 100. Preferably, the electrode array 320 is to be inserted into the scala tympani 102 so that the electrode contacts 32 face the modiolar wall of the cochlea. The modiolar wall is the inside wall of the spiraling scala tympani, i.e., the wall pointed to by the arrows 105.

To insert the electrode array 320 into the scala tympani, it is first necessary to make a cochleostomy 107, i.e., an opening or hole that provides access into the scala tympani. Such cochleostomy may have a substantially round shape, with a diameter D2, or oval or oblong shape, having a length d1 and a width d2, as shown in FIG. 7A.

Figure 7B:
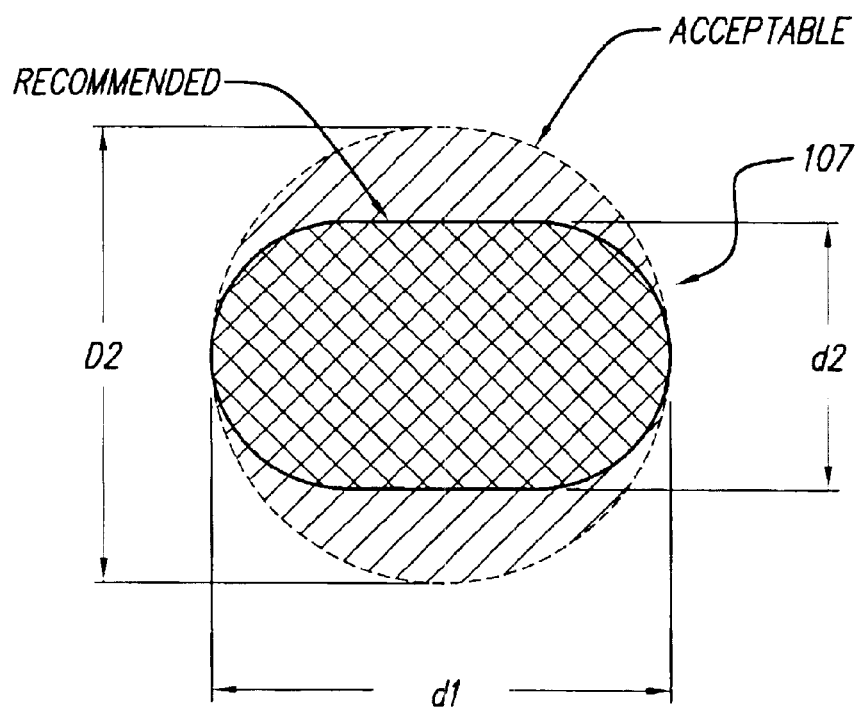
FIG. 7B illustrates preferred dimensions associated with the cochleostomy of FIG. 7A.

FIG. 7B illustrates the preferred size and shape of the cochleostomy 107. As seen in FIG. 7B, a recommended cochleostomy size and shape is an oval or oblong shape having a length di of approximately 1.5 mm and a height d2 of approximately 1.0 mm. However, it is also acceptable for the cochleostomy to be round, having a diameter D2 of approximately 1.5 mm. These dimensions are only very approximate, as the actual size may vary a great deal from insertion to insertion, and from patient to patient.

Figure 8A:
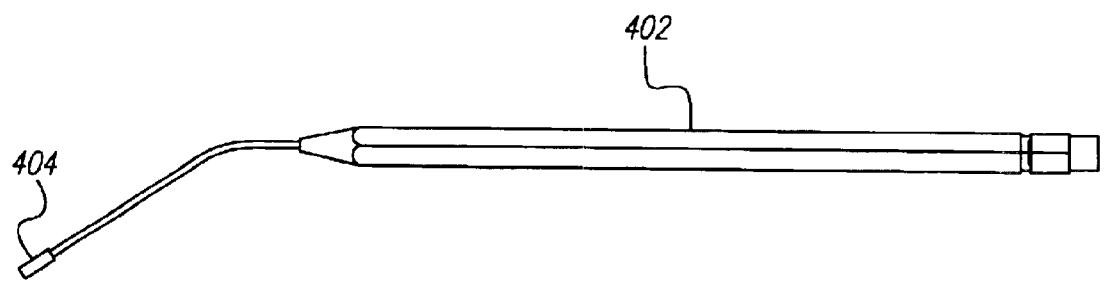
FIG. 8A illustrates a side view of an insertion gauge that may be used during insertion of the electrode system into the cochlea, and in particular to measure or check the size of the cochleostomy that has been made.
Figure 8B:
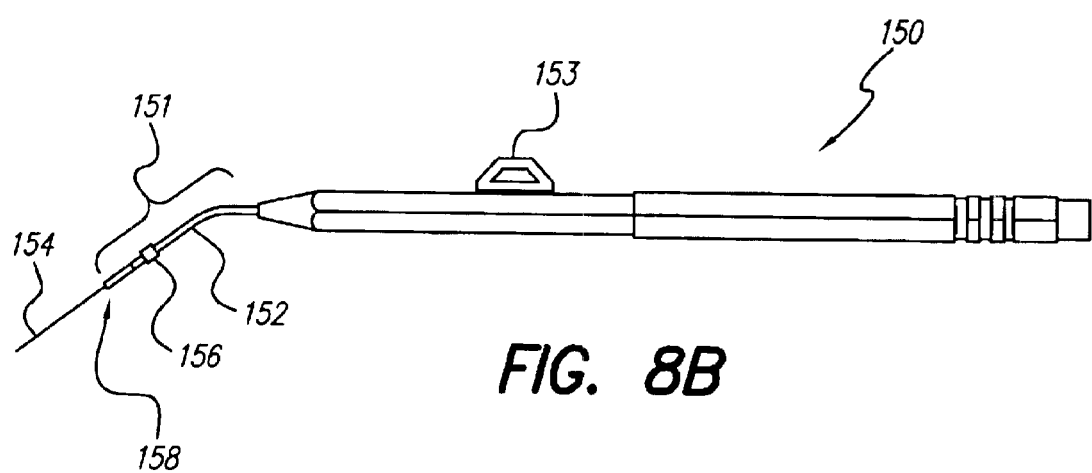
FIG. 8B is a side view of a preferred insertion tool that may be used to insert the electrode system into the cochlea.

An insertion gauge 402, shown in FIG. 8A, has a gauging tip 404 that defines the preferred size and shape of the cochleostomy needed in order to insert the electrode assembly. A cochleostomy, as is known to those of skill in the medical arts, comprises an opening or hole that is drilled, or otherwise made, through the bony tissue adjacent the round window. Once such cochleostomy has been made, the electrode system 300 of the present invention may be inserted into the scala tympani using an insertion tool 150 as shown in FIG. 8B. The insertion tool 150, shown in FIG. 8B, is used to insert the electrode array into the cochlea to the required depth. The insertion tool 150 has a tip portion 151 comprising a barrel tube 152 through which a stylet wire 154 extends. This barrel tube 152 may be slightly bent, and can swivel at its base to facilitate insertions of the electrode array into either a left or right cochlea. The barrel tube 152 has a tip collar 156 near its distal end 158. The stylet wire 154 may be extended or retracted as a function of the position of a slide tab 153. Advantageously, both the insertion gauge 402 and the insertion tool 150 are of a size that permits them to be easily held in one hand, between the fingers and thumb of a user, much like a pencil or pen.

Figure 9:
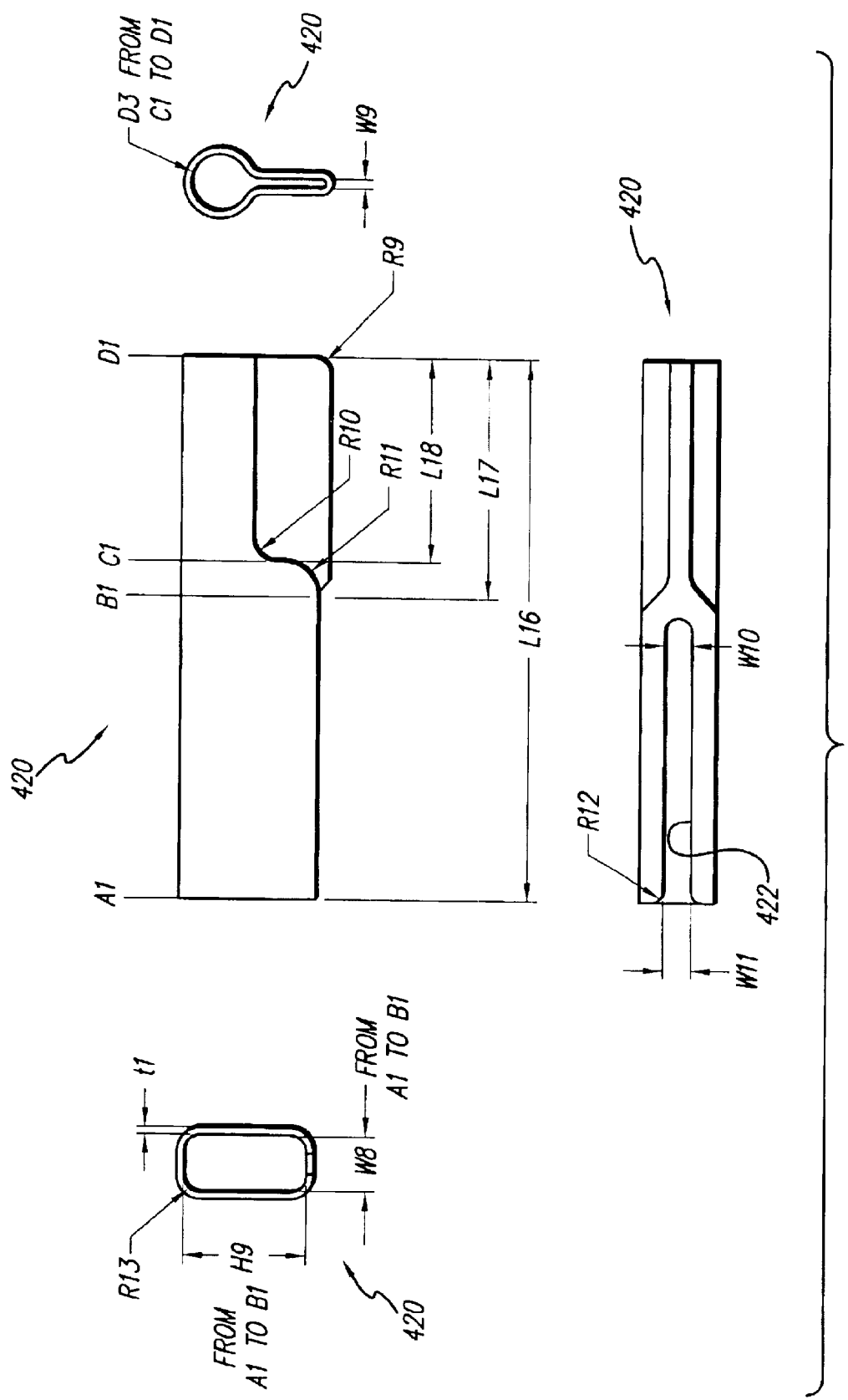
FIG. 9 is a mechanical drawing, showing side, end, and bottom views, of a preferred guiding tube used with the insertion tool of FIG. 8B during the insertion process.

Another tool used with the insertion tool 150 shown in FIG. 8 is a guiding tube 420 as shown in FIG. 9. The guiding tube 420 attaches to the end of the barrel tube 152 and helps maintain a stable orientation between the positioner 310 and electrode array 320 during the insertion process, as explained more fully below. At one end, as seen best on the right side of FIG. 9, the guiding tube 420 is formed to provide a tunnel, having a diameter D3, sized to fit snugly over the end of the barrel tube 152. At the other end, as seen best on the left side of FIG. 9, the guiding tube appears as an oval or oblong ring, having an inside width W8 and an inside height H9. This oval or oblong ring is adapted to receive the proximal end of both the electrode array 320 and the positioned 310, and has a slot 422 to accommodate the off-set 203' of the electrode array 320, as will be evident from the description that follows.

The guiding tube may be formed from a suitable metal tube, such as hypodermic tubing stainless steel, 11X gauge, thin wall, having an O.D. (outside diameter) of, e.g., 0.120 inches and an I.D. (inside diameter) of, e.g., 0.106 inches, thus providing a wall thickness of approximately 0.007 inches (7 thousands of an inch, or 7 mils). From a side view, as seen in the center of FIG. 9, the tube cross section (having diameter D3) extends from point D1 to point C1, where point D1 is at the right side of the guiding tube 420 and the point C1 is a distance L18 from D1. The oval or oblong cross section extends from point A1 to point B1, where point A1 is at the left side of the guiding tube and point B1 is a distance L17 from point D1. The guiding tube has a length, from point D1 to point A1, of LI6. The length between points B1 and C1 represents a transition area where the cross sectional shape changes from the oblong shape to the smaller tube shape. A slot 422, having a width W11 and a length that extends from point A1 to about point B1 is placed in the bottom of the guiding tube. The guiding tube is formed so as to be free from all sharp edges and burrs and is electro-polished to radius all edges. Representative dimensions for the guiding tube are shown in Table 2.

TABLE 2

Representative Dimensions of Guiding Tube 420 (FIG. 9)

| Dimension | Typical Value (inches) | Dimension | Typical Value (inches) |
|---|---|---|---|
| L16 | .591 ± 0.10 | W10 | .025 |
| L17 | .276 ± .005 | W11 | .029 + .000 − .004 |
| L18 | .220 ± 0.10 | R9 | .020 ± .010 |
| t1 | .007 | R10 | .020 ± .010 |
| D3 | .057 + .000 − .002 | R11 | .039 ± .010 |
| H9 | .132 | R12 | .015 |
| W8 | .065 | R13 | .024 |
| W9 | .008 | | |

In order to insert the electrode array into the cochlea, the following procedure is followed. First, the insertion gauge 402 should be sterilized by autoclaving for 30 minutes at 250° F. (121° C.). Next, the cochleostomy is made, using any suitable technique, and the gauging tip 404 of the insertion gauge 402 is used to verify the cochleostomy size. It is noted that a larger cochleostomy allows a deeper insertion of the positioner; however, at least 1 mm of the positioner should remain outside the cochleostomy.

Figure 10:
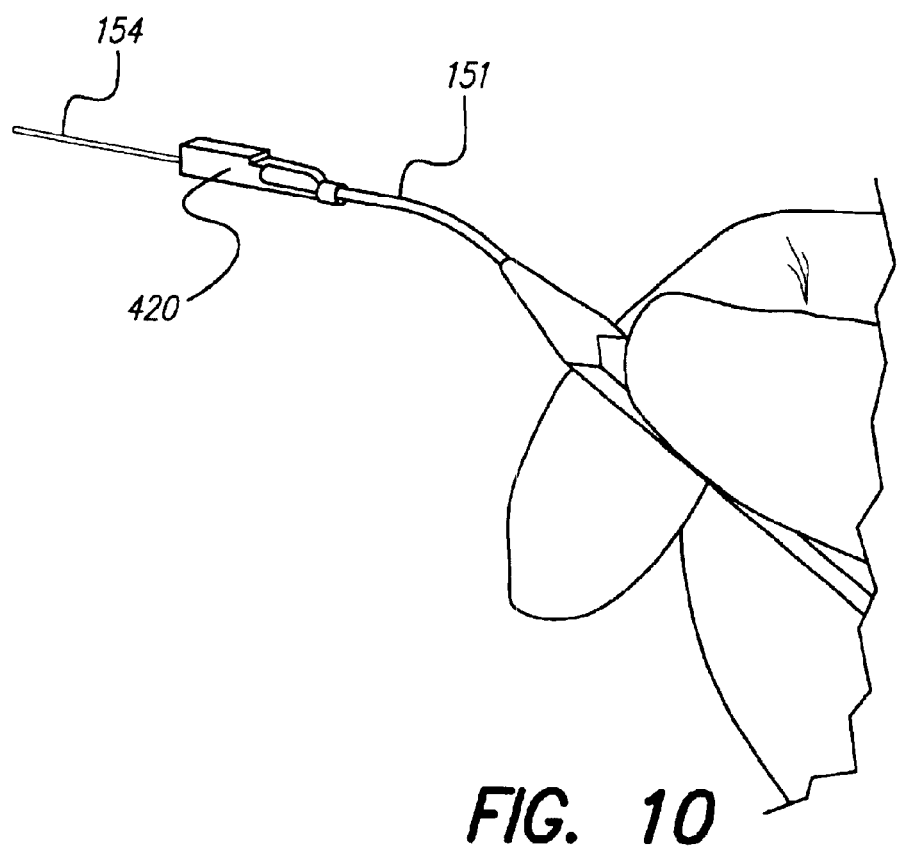
FIG. 10 illustrates the guiding tube of FIG. 9 detachably secured to the tip of the insertion tool of FIG. 8B.
Figure 12:
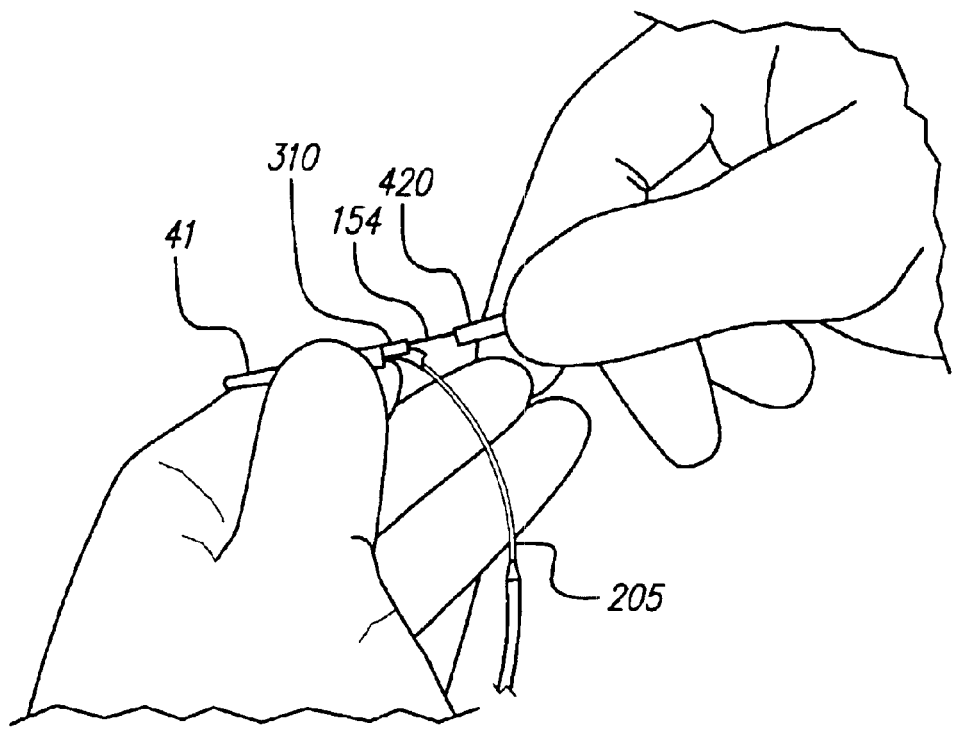
FIGS. 12, 13 and 14 illustrate the procedure for loading the proximal end of the electrode system into the guiding tube.
Figure 13:
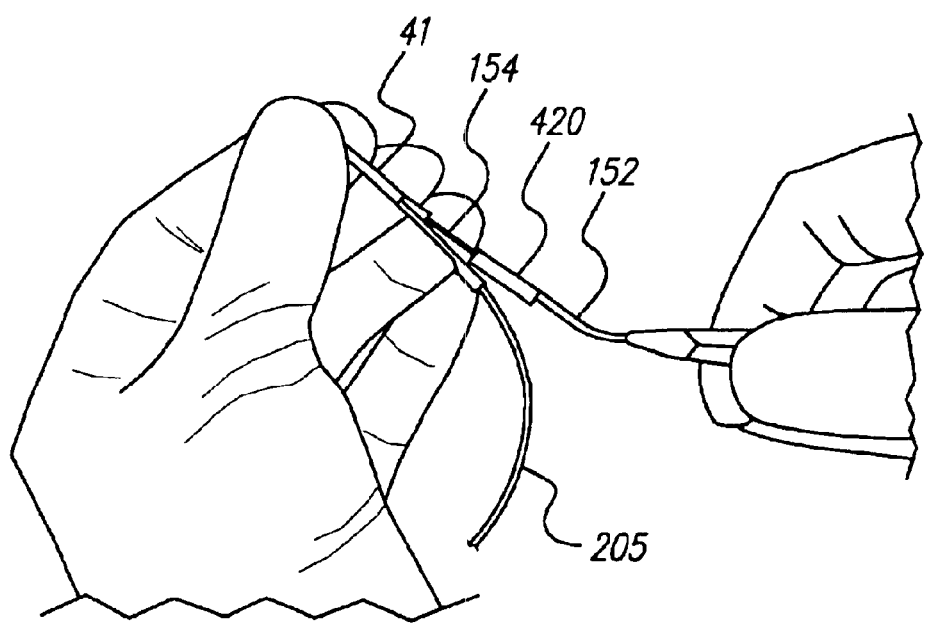

After a cochleostomy of the desired size has been made, the slide tab 153 on the insertion tool 150 is retracted. The guiding tube 420, which is also sterilized, is fitted onto the barrel 152 of the insertion tool, as seen in FIG. 10. The protruding stylet wire 154 is dipped in sterile saline or water. Then, the electrode array 320 is loaded into the insertion tool 150. This is accomplished by holding the insertion tool 150 at the barrel tube 152, e.g., near the tip collar 156, as seen in FIG. 12. The electrode array 320, while still inserted in its sheath 41, is held between the thumb and fingers of the other hand, as shown in FIG. 13, while the stylet wire 154 is inserted into the lumen 314 at the proximal end of the positioner 310. The stylet wire 154 Is inserted into the lumen of the positioner 320 until the distal tip of the wire reaches the sealed end of the positioner near its distal end and the proximal end of the positioner 310 and electrode array 320 are loaded into one end of the guiding tube 420, as shown in FIG. 14.

Figure 18:
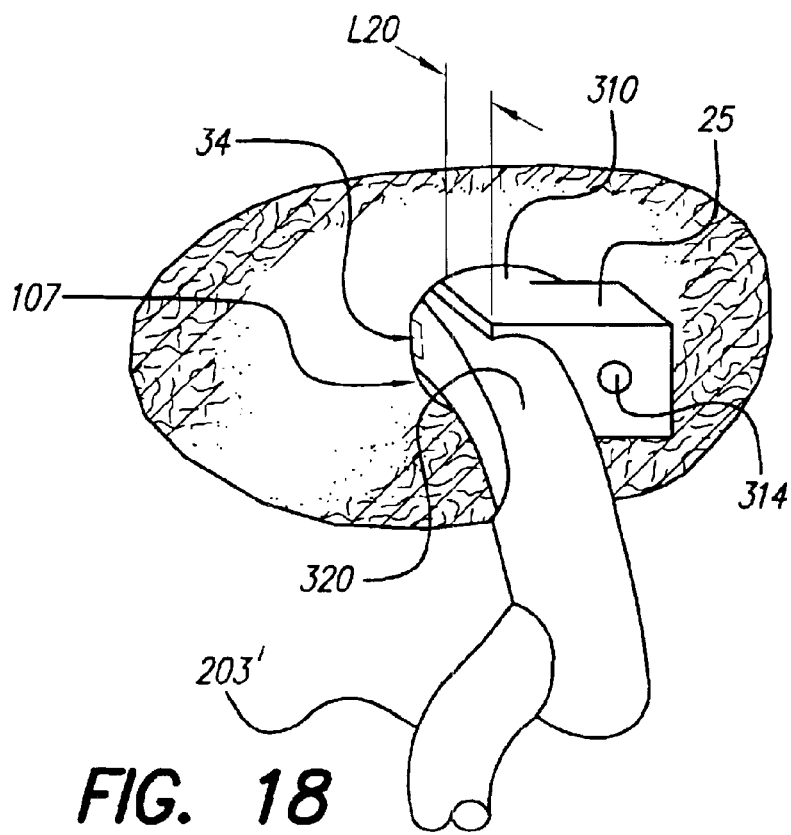
FIG. 18 illustrates a fully inserted electrode system as seen at the cochleostomy site.
Figure 11:
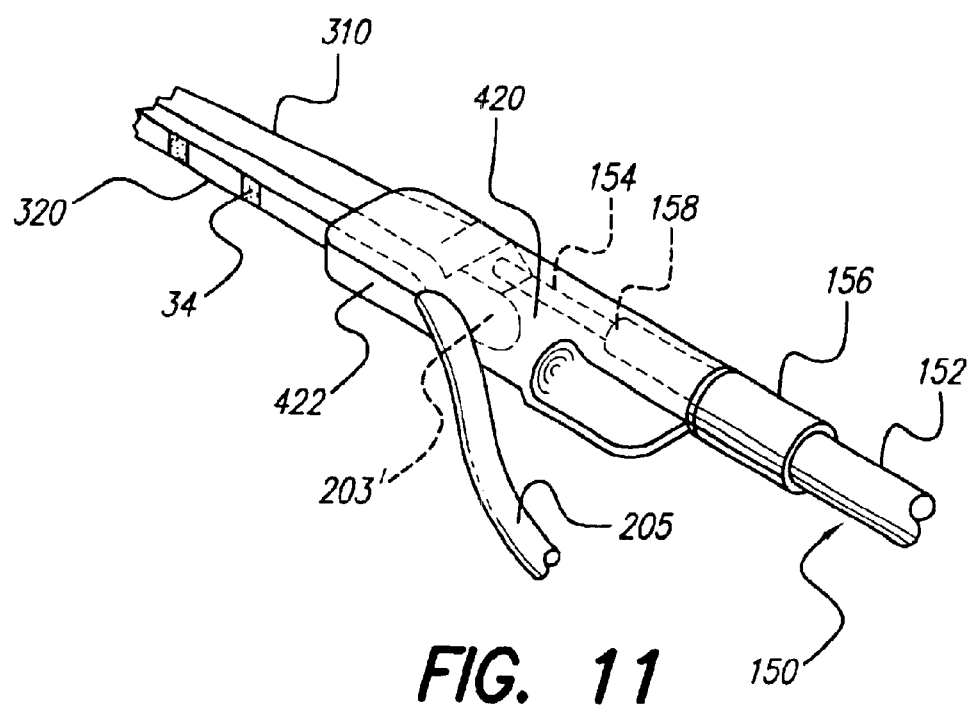
FIG. 11 shows a proximal end of the electrode system loaded into the guiding tube which is secured on the tip of the insertion tool.
Figure 14:
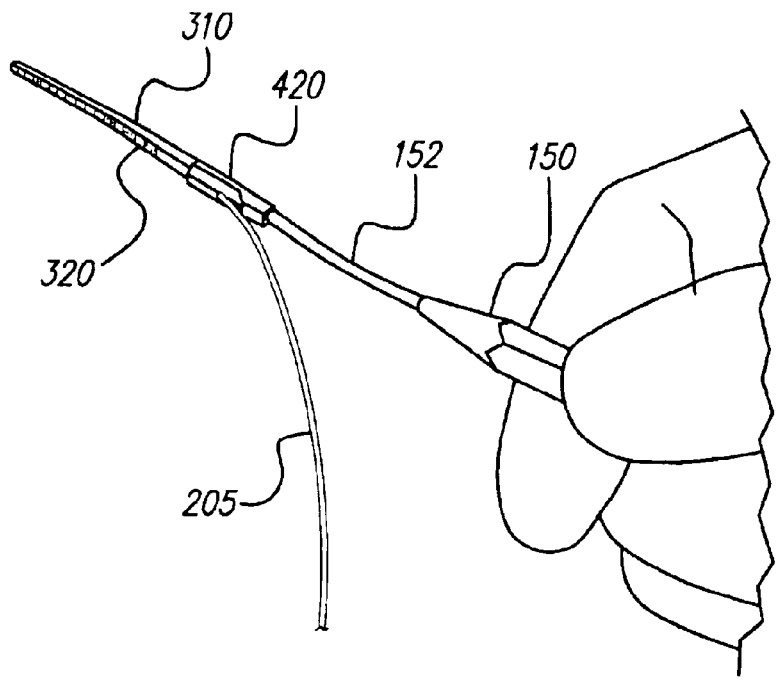
Figure 15:
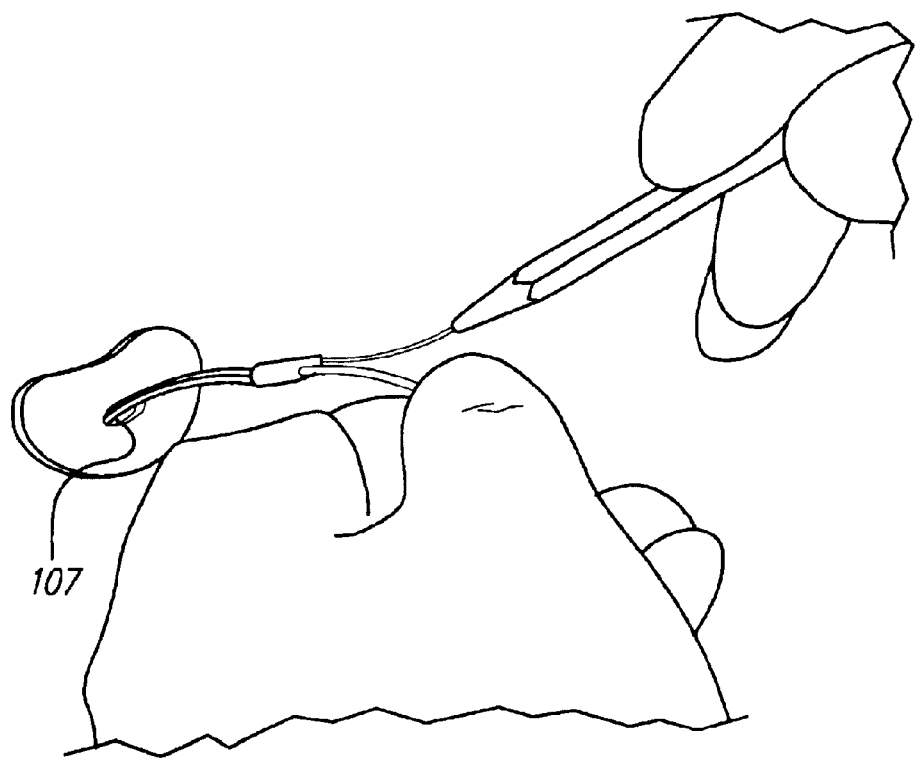
FIG. 15 illustrates the process of inserting the electrode system through the cochleostomy into the cochlea using the insertion tool and guiding tube.
Figure 16:
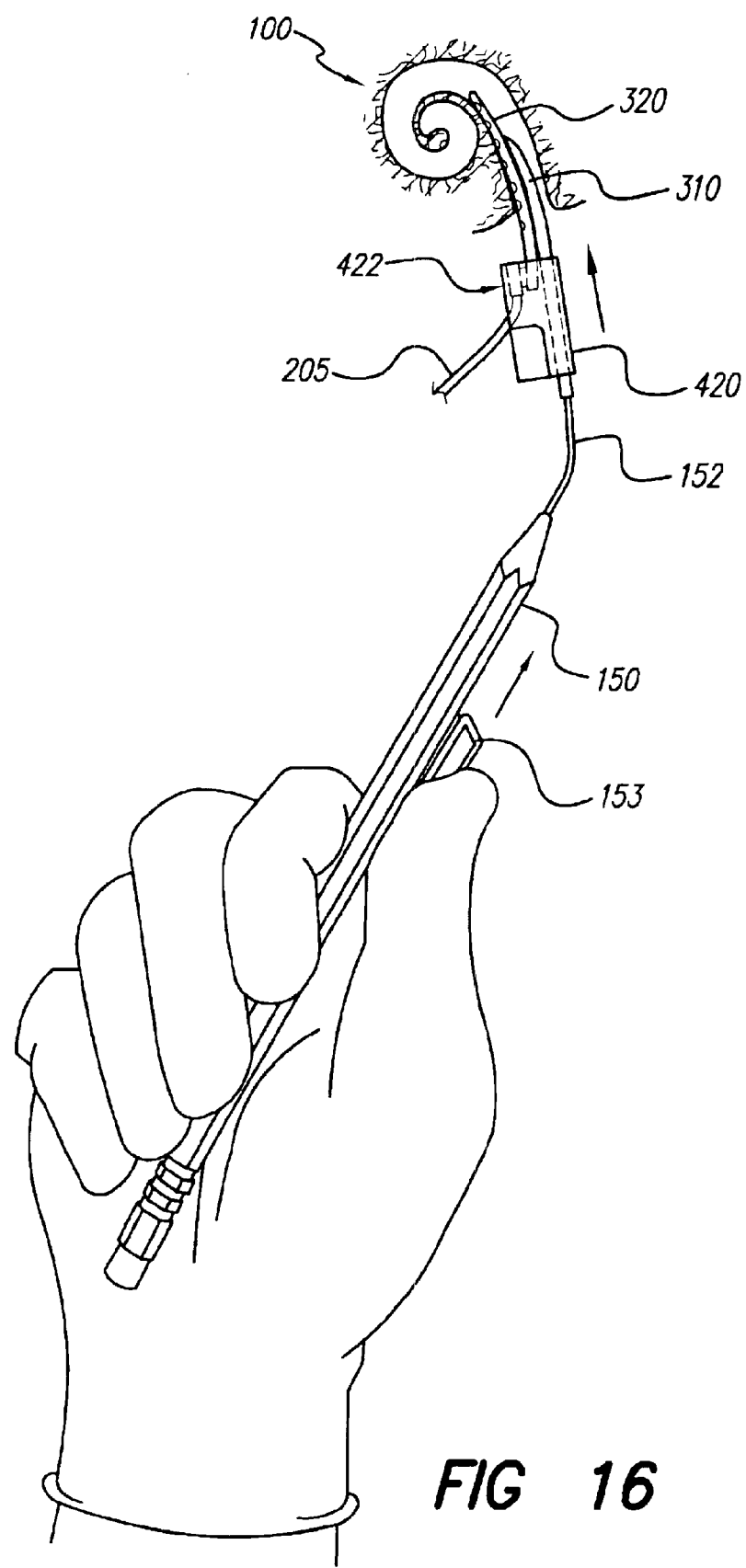
FIG. 16 schematically illustrates the insertion process as the electrode system begins its insertion Into the cochlea.

In the loaded position, shown in FIG. 11, and also represented in FIG. 14, the guiding tube 420 advantageously holds the electrode array 320 in a parallel position to the positioner 310 during the initial placement of the electrode assembly through the cochleostomy 107 into the cochlea. Such insertion is accomplished, as shown in FIGS. 15 and 16, by sliding the tab 153 on the insertion tool 150 in order to extend the stylet wire 154. Extension of the stylet wire 154 advances the positioner 310 and electrode array 320 into the scala tympani 102 of the cochlea 100. The parallel position between the electrode array 320 and the positioner 310 is maintained for the first 3–4 mm of insertion, which carries the electrode array and positioner past the first turn of the scala tympani. After reaching this point, the electrode array offset 203' disengages from the slot 422 of the guiding tube 420, allowing the electrode array 320 to be dragged into the scala tympani to the desired depth without being affected by torque form the lead 205. Advancement of the electrode array into the cochlea continues by slowly moving the slidable tab 153 on the insertion tool 150 forward, using the thumb, a distance L20, which means about 1 to 3 mm of the positioner 310 Is left outside the cochleostomy, or until internal resistance stops further insertion of the positioner. At this location, one or more of the reference contacts 34, if present on the electrode array, may still be visible, as shown in FIG. 18.

With the electrode array and positioner fully inserted into the cochlea, the insertion tool is retracted. As it is retracted, forward movement is maintained on the slider tab 153 until the stylet wire 154 disengages from the positioner. Then, the cochleostomy site should be inspected, and any gaps may be packed with muscle or fascia.

During the insertion process, as the positioner 310 is pushed deeper into the cochlea, the positioner body fills the space behind the electrode array 320, causing the electrode array 320 to hug the modiolar wall 105. This hugging of the modiolar wall, with the front surface of the electrode array facing the modiolar wall, further places the electrode contacts 32 near, or in contact with, the modiolar wall, as desired. Upon full insertion of the electrode array and positioner into the cochlea, the sloping floor 152 between the proximal side walls 316 (also known as "tapered wings") at the proximal end of the positioner, shown in FIG. 3, helps hold or wedge the electrode array 320 and positioner 310 firmly into the cochleostomy, thereby holding the electrode system 300 in place within the cochlea.

Figure 17:
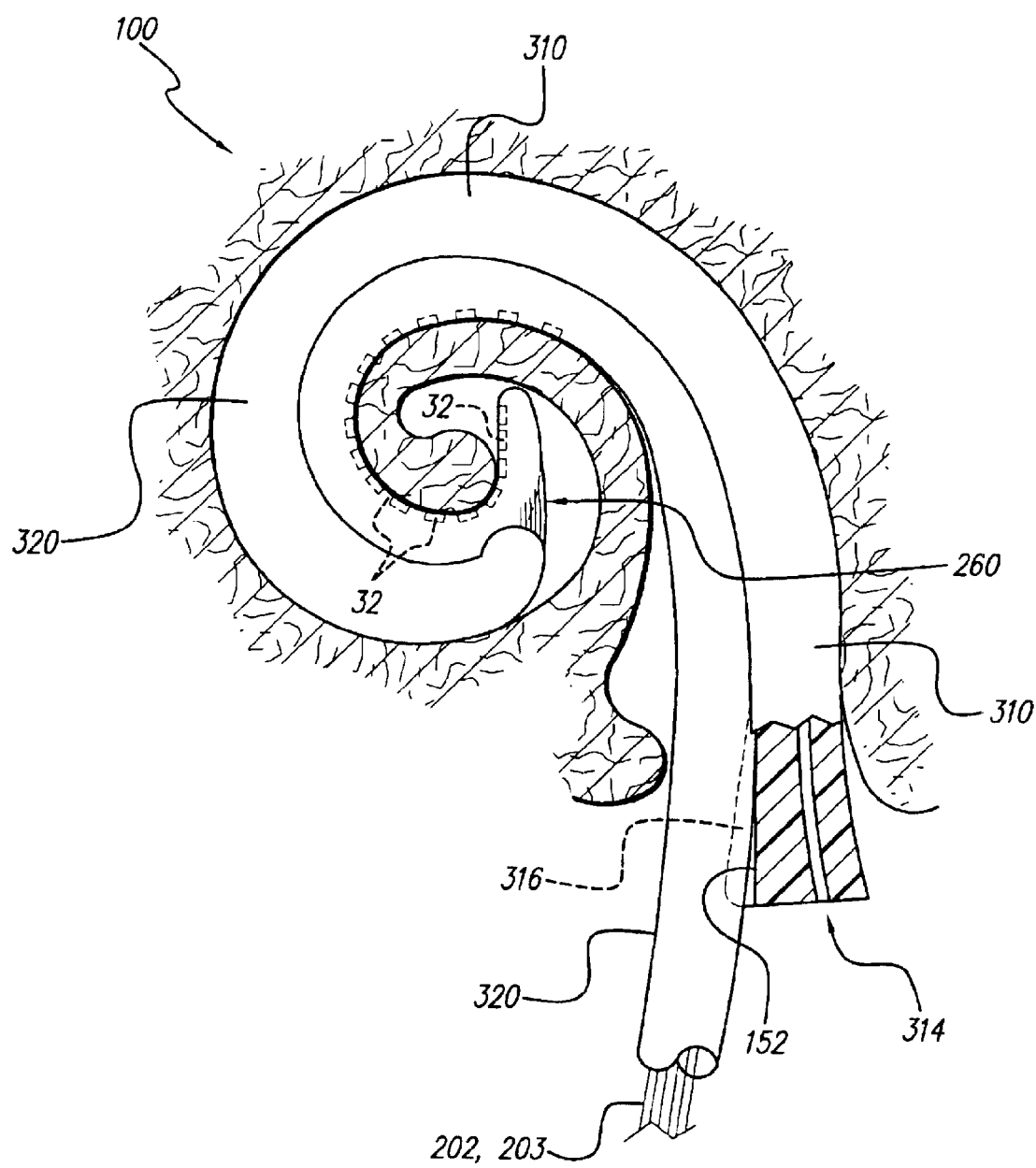
FIG. 17 schematically illustrates the electrode system fully inserted into the cochlea.

A schematic representation of the electrode array 320 and positioner 310 fully inserted into the cochlea is illustrated in FIG. 17. A proximal view of the electrode array 320 and positioner 310, fully Inserted into the scala tympani, as seen from the outside looking at the cochleostomy site 107, is shown in FIG. 18.

Hence, as shown in FIGS. 10–18, it is seen that through a single operation, i.e., extending the stylet wire 154 a prescribed amount, both the electrode array 320 and the positioner 310 are inserted into the scala tympani 102 of the cochlea 100 at the same time. When fully inserted, as shown in FIG. 17, both the electrode array 320 and the positioner 310 reside in their desired orientation within the scala tympani, with the electrode contacts 32 of the electrode array 320 hugging the modiolar wall, and with the positioner 320 filling the space behind the electrode array so as to force the electrode array snugly against the modiolar wall. When the electrode system is thus fully inserted, the stylet wire is removed from the longitudinal channel or lumen 314 of the positioner.

Advantageously, the entire process of inserting the electrode system 300 into the cochlea, as illustrated in FIGS. 10–18, can take place in a very short time. Further, during the actual insertion process, the distal tip of the electrode array, which leads the assembly as it slides into the scala tympani, acts as a bumper and guides the assembly deep into the cochlea, through the various spiraling turns of the scala tympani of the cochlea, without damaging or causing other significant trauma to the inside of the cochlea. For this reason, the carrier 36 of the electrode array 320, in accordance with the present invention, may be made entirely of a relatively soft material, e.g., LSR-25. Such material is a softer and more pliable material than has heretofore been used for the carrier of the electrode array when the electrode array must be inserted into the cochlea by itself without being an integral part of an electrode assembly 300.

As described above, it is thus seen that the electrode system of the present invention assures that the electrode contacts of the electrode array are optimally positioned facing the medial direction, e.g., facing the modiolar wall in a cochlea of any size or any side (left or right) of the body. Moreover, the electrode system assures the electrode contacts, or alternatively the non-conductive humps or bumps (if used) between the electrode contacts, are positioned against the modiolar wall. Additionally, it is seen that the electrode system may be easily inserted into the cochlea, and removed and reinserted, if required. Finally, it is seen that the invention provides a space-filling electrode system for use in the cochlea that may be readily inserted into the cochlea with minimal effort and without risk of undue injury, harm or trauma to the cochlea While the invention herein disclosed has been described by means of specific embodiments and applications thereof, numerous modifications and variations could be made thereto by those skilled in the art without departing from the scope of the invention set forth in the claims.

What is claimed is:

1. An insertion tool for use in inserting an electrode into a cochlea of a user, the electrode comprising a cochlear electrode array formed on an elongate flexible member having a longitudinal lumen passing therethrough, the longitudinal lumen being closed at its distal end, the insertion tool comprising:

a hand-held implantation tool having a body and a barrel, wherein the body has the approximate size and shape of a pen or pencil;

a protruding, extendable and retractable stylet wire passing through the barrel;

a slidable tab along one edge of the body of the tool, the tab being connected to the stylet wire, wherein imparting sliding movement to the tab cause the stylet wire to extend out of the barrel or retract into the barrel;

a guiding tube adapted to fit snugly on a distal tip of the barrel, the guiding tube having a distal end adapted to hold a proximal end of the electrode array as the insertion of the electrode array into the cochlea commences;

wherein the barrel of the insertion tool includes a bend in order to facilitate guiding the stylet wire into a left or right cochlea; and further wherein the barrel of the insertion tool is attached to the body of the insertion through a swivel connection, wherein the barrel may be rotated by way of the swivel connection relative to the body of the insertion tool in order to facilitate insertions of a stylet wire, with the electrode array threaded thereon, into either a left or a right cochlea;

wherein the lumen of the electrode array is adapted to be threaded onto the stylet wire prior to inserting the electrode array into the cochlea, and wherein the stylet wire is extended as the electrode array is inserted into a cochlea, and wherein the stylet wire is retracted from the electrode array once the electrode array has been inserted to a desired depth within the cochlea.

2. The insertion tool of claim 1 wherein the electrode array includes an offset portion at its proximal end where a lead attaches to the electrode array.

3. The insertion tool of claim 2 wherein the guiding tube includes a slot along one edge thereof adapted to receive the offset portion of the electrode array.

4. The insertion tool of claim 3 wherein the slot of the guiding tube holds the offset portion of the electrode array for the first 2–4 mm of insertion of the electrode array away into the cochlea.

5. A method for inserting a cochlear electrode into the cochlea of a patient, the cochlear electrode comprising a cochlear electrode array formed on an elongate flexible member having a longitudinal lumen passing therethrough, the lumen channel being closed at its distal end; the method comprising:

(a) inserting the electrode array into a sheath;

(b) while holding the sheath in one hand, inserting a flexible stylet wire into the lumen of the cochlear electrode until a distal tip of the stylet wire engages the closed distal end of the lumen channel;

(c) while holding the stylet wire, removing the sheath from the electrode array, (d) positioning a distal end of the cochlear electrode within an opening of the cochlea so that the electrode array is closest to a modlolar wall of the cochlea;

(e) extending the stylet wire forward a prescribed distance, thereby pushing the cochlear electrode into the cochlea a distance equal to the prescribed distance; and (f) removing the stylet wire.

6. The method of claim 5 further including guiding the stylet wire through a guiding tube prior to inserting it into the lumen of the cochlear electrode;

inserting a proximal end of the electrode array into the a distal end of the guiding tube, the guiding tube serving the function of holding the electrode array as the electrode array is inserted into the cochlea.

* * * * *